US008658433B2

(12) United States Patent
Rajagopalan et al.

(10) Patent No.: US 8,658,433 B2
(45) Date of Patent: *Feb. 25, 2014

(54) DYE COMPOUNDS AS PHOTOACTIVE AGENTS

(75) Inventors: Raghavan Rajagopalan, Beechwood, OH (US); Gary L. Cantrell, Troy, IL (US); Samuel I. Achilefu, St. Louis, MO (US); Joseph E. Bugaj, St. Charles, MO (US); Richard B. Dorshow, St. Louis, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 1292 days.

This patent is subject to a terminal disclaimer.

(21) Appl. No.: 11/931,683

(22) Filed: Oct. 31, 2007

(65) Prior Publication Data

US 2008/0139786 A1 Jun. 12, 2008

Related U.S. Application Data

(60) Continuation of application No. 10/776,840, filed on Feb. 11, 2004, now Pat. No. 7,303,926, and a division of application No. 09/898,885, filed on Jul. 3, 2001, now abandoned, and a continuation of application No. 10/685,172, filed on Oct. 14, 2003, now Pat. No. 7,230,088, and a continuation-in-part of application No. 09/898,885, filed on Jul. 3, 2001, now abandoned, and a continuation of application No. 11/277,057, filed on Mar. 21, 2006, now Pat. No. 7,758,861, and a continuation of application No. 09/898,809, filed on Jul. 3, 2001, now Pat. No. 7,351,807, and a continuation-in-part of application No. 09/484,322, filed on Jan. 18, 2000, now Pat. No. 6,395,257, and a continuation of application No. 10/808,184, filed on Mar. 24, 2004, now abandoned, and a division of application No. 09/766,347, filed on Jan. 19, 2001, now abandoned, and a continuation of application No. 11/276,971, filed on Mar. 20, 2006, now Pat. No. 7,427,657, and a continuation of application No. 09/898,887, filed on Jul. 3, 2001, now Pat. No. 7,235,685.

(51) Int. Cl.
G01N 33/532 (2006.01)
G01N 33/533 (2006.01)
C07K 1/13 (2006.01)
A61K 39/395 (2006.01)

(52) U.S. Cl.
USPC ..... 436/544; 424/178.1; 436/546; 530/391.7; 530/405

(58) Field of Classification Search
None
See application file for complete search history.

(56) References Cited

U.S. PATENT DOCUMENTS

| 3,887,379 | A | | 6/1975 | Clecak et al. |
| 5,214,036 | A | * | 5/1993 | Allison et al. ................ 514/185 |
| 5,460,801 | A | * | 10/1995 | Cuttitta et al. ............. 424/138.1 |
| 5,563,132 | A | * | 10/1996 | Bodaness ...................... 514/185 |
| 6,217,848 | B1 | * | 4/2001 | Achilefu et al. ............... 424/9.1 |
| 6,313,274 | B1 | * | 11/2001 | Sykes et al. ................. 530/391.3 |
| 6,962,686 | B2 | * | 11/2005 | Kayyem et al. .............. 424/1.69 |
| 7,230,088 | B2 | * | 6/2007 | Rajagopalan et al. ........ 530/405 |
| 7,303,926 | B2 | * | 12/2007 | Rajagopalan et al. ........ 436/546 |
| 7,351,807 | B2 | * | 4/2008 | Rajagopalan et al. ........ 530/408 |
| 2003/0216795 | A1 | * | 11/2003 | Harth et al. ..................... 607/88 |
| 2004/0180864 | A1 | * | 9/2004 | Rajagopalan et al. ........ 514/151 |
| 2006/0177457 | A1 | * | 8/2006 | Rajagopalan et al. ..... 424/178.1 |

FOREIGN PATENT DOCUMENTS

| JP | 2003-509836 | 2/2005 |
| WO | 00/12512 | 3/2000 |

OTHER PUBLICATIONS

Pinney et al. Efficient and selective photoaffinity labeling of the estrogen receptor using two nonsteroidal ligands that embody aryl azide or tetrafluoroaryl azide photoreactive functions. Biochemistry 1991, vol. 30, pp. 2421-2431.*
Pandurangi et al. Chemistry of bifunctional photoprobes.1 3. correlation between the efficiency of CH insertion by photolabile chelating agents and lifetimes of singlet nitrenes by flash photolysis: first example of photochemical attachment of 99mTc-complex with human serum albumin. J. Org. Chem. 1998, vol. 63, pp. 9019-9030.*
Kym et al. Evaluation of a high efficient aryl azide photoaffinity labeling reagent for the progesteron receptor. Bioconjugate Chem. 1995, vol. 6, pp. 115-122.*
International Search Report issued in connection with PCT/GB99/02864. Jan. 17, 2000. pp. 1-6.
Japanese Patent Office Office Action, patent application No. 2003-509836. Date: Feb. 13, 2009. Mailed Feb. 20, 2009. (English translation provided.).
Pochinok, V., et al., Photochemistry of Azide Group-Containing Dyes in Solution, Ukrainskij Khimicheskij Zhurnal,, 1984, 50(3), pp. 296-301. (English translation not provided.).

(Continued)

Primary Examiner — Shafiqul Haq
(74) Attorney, Agent, or Firm — Thompson Hine LLP

(57) ABSTRACT

Novel azo, azide, and sulfenate photoactive compounds and methods using the compounds for photodiagnostic and/or phototherapeutic procedures. The compounds have the formula E-L-DYE-X—Y, wherein DYE is a photoactive component comprising a photoactive diagnostic agent, a photoactive type 1 agent, a photoactive type 2 agent, or a combination thereof;

Y is a photoactive component comprising a photoactive type 1 agent, a photoactive type 2 agent, or a combination thereof;

E is a targeting component for targeting the compound to an anatomical and/or physiological site of a patient;

L is a linking component for linking E to DYE; and

X is a linking component for linking DYE to Y.

2 Claims, 18 Drawing Sheets

(56) References Cited

OTHER PUBLICATIONS

Japanese Laid-Open Publication No. 49-17223, Feb. 15, 1974. (Translators Note: There is no English language counterpart application).

Ol'Shevskaya, I., Khim. Geterotsikl, Soedin., Synthesis and Reactions of Azides of Heterocyclic Compounds, May 1974, No. 5, pp. 640-642.

* cited by examiner

DYE COMPOUNDS AS PHOTOACTIVE AGENTS

RELATED APPLICATIONS

This application is a Continuation of U.S. patent application Ser. No. 10/776,840 (filed Feb. 11, 2004), now U.S. Pat. No. 7,303,926; which is a division of Ser. No. 09/898,885 (filed Jul. 3, 2001, abandoned); and of Ser. No. 10/685,172 (filed Oct. 14, 2003) now U.S. Pat. No. 7,230,088, which is a continuation-in-part of Ser. No. 09/898,885 (filed Jul. 3, 2001; abandoned); Ser. No. 11/277,057 (filed Mar. 21, 2006), now U.S. Pat. No. 7,758,861, which is a continuation of Ser. No. 09/898,809 (filed Jul. 3, 2001) now U.S. Pat. No. 7,351,807, which is a continuation-in-part of Ser. No. 09/484,322 (filed Jan. 18, 2000), now U.S. Pat. No. 6,395,257; Ser. No. 10/808,184 (filed Mar. 24, 2004), abandoned, which is a division of Ser. No. 09/766,347 (filed Jan. 19, 2001; abandoned); Ser. No. 11/276,971 (filed Mar. 20, 2006), now U.S. Pat. No. 7,427,657, which is a continuation of Ser. No. 09/898,887 (filed Jul. 3, 2001), now U.S. Pat. No. 7,235,685; the disclosure of each hereby incorporated by reference in its entirety.

TECHNICAL FIELD

Novel azo, azide, and sulfenate photoactive compounds for photodiagnostic and/or phototherapeutic procedures.

BACKGROUND

The use of visible and near-infrared (NIR) light in clinical practice is growing rapidly. Compounds absorbing or emitting in the visible or NIR, or long-wavelength (ultraviolet-A (UV-A)>350 nm) region of the electromagnetic spectrum are potentially useful for optical tomographic imaging, endoscopic visualization, and phototherapy. However, a major advantage of biomedical optics lies in its therapeutic potential. Phototherapy has been demonstrated to be a safe and effective procedure for the treatment of various surface lesions, both external and internal. Its efficacy is akin to radiotherapy, but it advantageously lacks the harmful radiotoxicity to critical non-target organs.

Phototherapy has been in existence for many centuries and has been used to treat various skin surface ailments. As early as 1400 B.C. in India, plant extracts (psoralens), in combination with sunlight, were used to treat vitiligo. In 1903, Von Tappeiner and Jesionek used eosin as a photosensitizer for treating skin cancer, lupus of the skin, and condylomata of female genitalia. Over the years, the combination of psoralens and UV-A (low-energy) radiation has been used to treat a wide variety of dermatological diseases and manifestations including psoriasis, parapsoriasis, cutaneous T-cell lymphoma, eczema, vitiligo, greata, and neonatal bilirubinemia. Although the potential of cancer phototherapy has been recognized since the early 1900's, systematic studies to demonstrate safety and efficacy began only in 1967 with the treatment of breast carcinoma. In 1975, Dougherty et al. conclusively established that long-term cure is possible with photodynamic therapy (PDT). Currently, phototherapeutic methods are also being investigated for the treatment of some cardiovascular disorders such as atherosclerosis and vascular restenosis, for the treatment of rheumatoid arthritis, and for the treatment of some inflammatory diseases such as Chron's disease.

Phototherapeutic procedures require photosensitizers (i.e. chromophores) having high absorptivity. These compounds should preferably be chemically inert, and become activated only upon irradiation with light of an appropriate wavelength. Selective tissue injury can be induced with light when photosensitizers bind to the target tissues, either directly or through attachment to a bioactive carrier. Furthermore, if the photosensitizer is also a chemotherapeutic agent (e.g., anthracycline antitumor agents), then an enhanced therapeutic effect can be attained. The key requirements for the design of effective phototherapeutic agents are: (a) large molar extinction coefficients, (b) long triplet lifetimes, (c) high yields of singlet oxygen and/or other reactive intermediates, viz., free radicals, nitrenes, carbenes, or open-shell ionic species such as carbonium ions and the like, (d) efficient energy or electron transfer to cellular components, (e) low tendency to form aggregation in an aqueous milieu, (f) efficient and selective targeting of lesions, (g) rapid clearance from the blood and non-target tissues, (h) low systemic toxicity, and (i) lack of mutagenicity.

Photosensitizers operate via two distinct mechanisms, termed Types 1 and 2. The type 1 mechanism is shown in the following scheme:

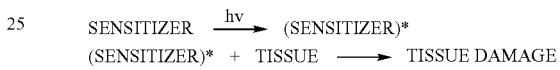

Type 1 mechanisms involve direct energy or electron transfer from the photosensitizer to the cellular components thereby causing cell death. Type 2 mechanisms involve two distinct steps, as shown in the following scheme:

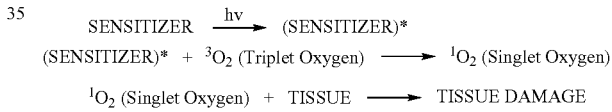

In the first step, singlet oxygen is generated by energy transfer from the triplet excited state of the photosensitizer to the oxygen molecules surrounding the tissues. In the second step, collision of singlet oxygen with the tissues promotes tissue damage. In both Type 1 and Type 2 mechanisms, the photoreaction proceeds via the lowest triplet state of the photosensitizer. Hence, a relatively long triplet lifetime is required for effective phototherapy. In contrast, a relatively short triplet lifetime is required to avoid photodamage to the tissue caused by photosensitizers.

The biological basis of tissue injury brought about by tumor phototherapeutic agents has been the subject of intensive study. Various biochemical mechanisms for tissue damage have been postulated even though the type and number of photosensitizers employed in these studies are relatively small. These biochemical mechanisms are as follows: (a) cancer cells upregulate the expression of low density lipoprotein (LDL) receptors, and PDT agents bind to LDL and albumin selectively; (b) porphyrin-like substances are selectively taken up by proliferative neovasculature; (c) tumors often contain increased number of lipid bodies and are thus able to bind to hydrophobic photosensitizers; (d) a combination of "leaky" tumor vasculature and reduced lymphatic drainage causes porphyrin accumulation; (e) tumor cells may have increased capabilities for phagocytosis or pinocytosis of porphyrin aggregates; (f) tumor associated macrophages may be largely responsible for the concentration of photosensitizers in tumors; and (g) cancer cells may undergo apoptosis induced by photosensitizers. Among these mechanisms, (f) and (g) are the most general and, of these two alternatives, there is a general consensus that (f) is the most likely mechanism by which the phototherapeutic effect of porphyrin-like compounds is induced.

Most of the currently known photosensitizers are commonly referred to as PDT agents and operate via the Type 2 mechanism. For example, Photofrin II (a hematoporphyrin derivative) has been approved by the U.S. Food and Drug Administration for the treatment of bladder, esophageal, and late-stage lung cancers. However, Photofrin II has been shown to have several drawbacks: a low molar absorptivity ($\epsilon$=3000 M$^{-1}$), a low singlet oxygen quantum yield ($\phi$=0.1), chemical heterogeneity, aggregation, and prolonged cutaneous photosensitivity. Hence, there has been considerable effort in developing safer and more effective photosensitizers for PDT which exhibit improved light absorbance properties, better clearance, and decreased skin photosensitivity compared to Photofrin II. These include monomeric porphyrin derivatives, corrins, cyanines, phthalocyanines, phenothiazines, rhodamines, hypocrellins, and the like. However, these phototherapeutic agents also mainly operate via the Type 2 mechanism.

Surprisingly, there has not been much attention directed at developing Type 1 phototherapeutic agents, despite the fact that the Type 1 mechanism appears to be inherently more efficient than the Type 2 mechanism. First, unlike Type 2, Type 1 photosensitizers do not require oxygen for causing cellular injury. Second, the Type 1 mechanism involves two steps (photoexcitation and direct energy transfer), whereas the Type 2 mechanism involves three steps (photoexcitation, singlet oxygen generation, and energy transfer). Furthermore, certain tumors have hypoxic regions, which render the Type 2 mechanism ineffective. However, in spite of the drawbacks associated with the Type 2 mechanism, only a small number of compounds have been developed that operate through the Type 1 mechanism, e.g. anthracycline antitumor agents.

Thus, there is a need to develop effective phototherapeutic agents. Phototherapeutic efficacy can be substantially improved if both Type 1 and Type 2 units are integrated into a single composition. This can be accomplished using three types of formulations: (a) homogeneous mixtures of Type 1 or Type 2 agents alone, (b) heterogeneous mixtures of Type 1 and Type 2 agents, or (c) a single molecular entity containing both Type 1 and Type 2 functionalities.

SUMMARY

Novel azo, azide, and sulfenate photoactive compounds and methods using the compounds for photodiagnostic and/or phototherapeutic procedures. The compounds have the formula E-L-DYE-X—Y, wherein DYE is a photoactive component comprising a photoactive diagnostic agent, a photoactive type 1 agent, a photoactive type 2 agent, or a combination thereof;

Y is a photoactive component comprising a photoactive type 1 agent, a photoactive type 2 agent, or a combination thereof;

E is a targeting component for targeting the compound to an anatomical and/or physiological site of a patient;

L is a linking component for linking E to DYE; and

X is a linking component for linking DYE to Y.

In one embodiment, the present invention discloses novel compounds including organic azides, for phototherapy of tumors and other lesions, having the formula

where DYE is an aromatic or a heteroaromatic radical derived from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, and indolenium dyes; or the formula:

where Ar is a chromophore that undergoes sensitization and is an aromatic or a heteroaromatic radical derived from the group consisting of benzenes, polyfluorobenzenes, naphthalenes, naphthoquinones, anthracenes, anthraquinones, phenanthrenes, tetracenes, naphthacenediones, pyridines, quinolines, isoquinolines, indoles, isoindoles, pyrroles, imidazoles, pyrazoles, pyrazines, purines, benzimidazoles, benzofurans, dibenzofurans, carbazoles, acridines, acridones, phenanthridines, thiophenes, benzothiophenes, dibenzothiophenes, xanthenes, xanthones, flavones, coumarins, and anthracyclines.

In all azide embodiments, $N_3$ is the azide moiety that produces nitrene upon photoactivation, i.e., a photoactive component;

L is a linker, i.e., linking unit or linking component, between the DYE or chromophore and the targeting moiety E epitope that targets the compound to a particular anatomical and/or physiological site in a patient, and is selected from the group consisting of —(CH$_2$)$_a$—, —(CH$_2$)$_b$CONR$^1$—, —N(R$^2$)CO(CH$_2$)$_n$—, —OCO(CH$_2$)$_d$—, —(CH$_2$)$_e$CO$_2$—, —OCONH—, —OCO$_2$—, —HNCONH—, —HNCSNH—, —HNNHCO—, —OSO$_2$—, —NR$^3$(CH$_2$)$_e$CONR$^4$—, —CONR$^5$(CH$_2$)$_f$NR$^6$CO—, and —NR$^7$CO(CH$_2$)$_g$CONR$^8$—;

X is a linking unit or linking component that is either a single bond or is selected from the group consisting of —(CH$_2$)$_h$—, —OCO—, —HNCO—, —(CH$_2$)$_i$CO—, and —(CH$_2$)$_j$OCO—;

R$^1$ to R$^8$ are independently selected from the group consisting of hydrogen, C1-C10 alkyl, —OH, C1-C10 polyhydroxyalkyl, C1-C10 alkoxyl, C1-C10 alkoxyalkyl, —SO$_3$H, —(CH$_2$)$_k$CO$_2$H, and —(CH$_2$)$_l$NR$^9$R$^{10}$;

R$^9$ and R$^{10}$ are independently selected from the group consisting of hydrogen, C1-C10 alkyl, C5-C10 aryl, and C1-C10 polyhydroxyalkyl;

a to l independently range from 0 to 10;

and the targeting moiety E epitope is selected from the group consisting of somatostatin receptor binding molecules, ST receptor binding molecules, neurotensin receptor binding molecules, bombesin receptor binding molecules, cholecystekinin (CCK) receptor binding molecules, steroid receptor binding molecules, and carbohydrate receptor binding molecules.

In one embodiment, the present invention discloses novel sulfenate derivatives and their bioconjugates, for phototherapy of tumors and other lesions, having the formula

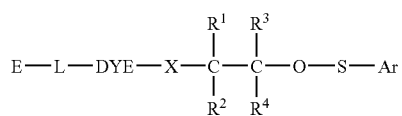

or the formula

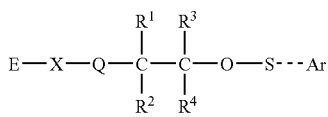

In all embodiments of sulfenates,

E is selected from the group consisting of somatostatin receptor binding molecules, ST receptor binding molecules, neurotensin receptor binding molecules, bombesin receptor binding molecules, CCK receptor binding molecules, steroid receptor binding molecules, and carbohydrate receptor binding molecules, and dihydroxyindolecarboxylic acid; and Ar is an aromatic or heteroaromatic radical derived from the group consisting of benzenes, naphthalenes, naphthoquinones, diphenylmethanes, fluorenes, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthracyclines.

When the sulfenate has the formula

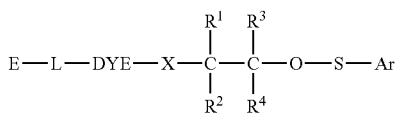

L and X are independently selected from the group consisting of —(R$^5$)NOC—, —(R$^5$)NOCCH$_2$O—, —(R$^5$)NOCCH$_2$CH$_2$O—, —OCN(R$^5$)—, —HNC(=S)NH—, and HNC(=O)NH—; and DYE is an aromatic or a heteroaromatic radical derived from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, indolenium dyes, crellins, and hypocrellins.

When the sulfenate has the formula

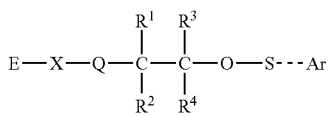

X is selected from the group consisting of —(R$^5$)NOC—, —(R$^5$)NOCCH$_2$O—, —(R$^5$)NOCCH$_2$CH$_2$O—, and —HNC(=S)NH; and Q is either a single bond or an alkenyl, aromatic, or heteroaromatic radical derived from a compound selected from the group consisting of olefins, benzenes, naphthalenes, naphthoquinones, fluorines, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines.

In all embodiments of sulfenates, $R^1$ to $R^5$ are independently selected from the group consisting of hydrogen, C1-C10 alkyl, C5-C10 aryl, C1-C10 polyhydroxyalkyl, and C1-C10 polyalkoxyalkyl.

The present invention also discloses a method of performing a phototherapeutic procedure using the disclosed azide compounds. An effective amount of organic azide photosensitizer is administered to a subject, where the organic azide photosensitizer has either the formula

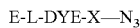

where DYE is an aromatic or a heteroaromatic radical derived from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, and indolenium dyes; or the formula

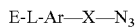

where Ar is an aromatic or a heteroaromatic radical derived from the group consisting of benzenes, polyfluorobenzenes, naphthalenes, naphthoquinones, anthracenes, anthraquinones, phenanthrenes, tetracenes, naphthacenediones, pyridines, quinolines, isoquinolines, indoles, isoindoles, pyrroles, imidiazoles, pyrazoles, pyrazines, purines, benzimidazoles, benzofurans, dibenzofurans, carbazoles, acridines, acridones, phenanthridines, thiophenes, benzothiophenes, dibenzothiophenes, xanthenes, xanthones, flavones, coumarins, and anthacylines.

In all azide embodiments, E is a hydrogen atom or is selected from the group consisting of somatostatin receptor binding molecules, ST receptor binding molecules, neurotensin receptor binding molecules, bombesin receptor binding molecules, CCK receptor binding molecules, steroid receptor binding molecules, and carbohydrate receptor binding molecules;

L is selected from the group consisting of —(CH$_2$)$_a$—, —(CH$_2$)$_b$CONR$^1$—, —N(R$^2$)CO(CH$_2$)$_c$—, —OCO(CH$_2$)$_d$—, —(CH$_2$)$_e$CO$_2$—, —OCONH—, —OCO$_2$—, —HNCONH—, —HNCSNH—, —HNNHCO—, —OSO$_2$—, —NR$^3$(CH$_2$)$_e$CONR$^4$—, —CONR$^5$(CH$_2$)$_f$NR$^6$CO—, and —NR$^7$CO(CH$_2$)$_g$CONR$^8$—;

X is either a single bond or is selected from the group consisting of —(CH$_2$)$_h$—, —OCO—, —HNCO—, —(CH$_2$)$_i$CO—, and —(CH$_2$)$_j$OCO—;

$R^1$ to $R^8$ are independently selected from the group consisting of hydrogen, C1-C10 alkyl, —OH, C1-C10 polyhydroxyalkyl, C1-C10 alkoxyl, C1-C10 alkoxyalkyl, —SO$_3$H, —(CH$_2$)$_k$CO$_2$H, and —(CH$_2$)$_l$NR$^9$R$^{10}$;

$R^9$ and $R^{10}$ are independently selected from the group consisting of hydrogen, C1-C10 alkyl, C5-C10 aryl, and C1-C10 polyhydroxyalkyl; and a to l independently range from 0 to 10.

Following administration, the photosensitizer is allowed to accumulate in target tissue which is exposed to a light of wavelength between 300 and 950 nm. This light has sufficient power and fluence rate to cause necrosis or apoptosis of the target tissue. The photoexcitation of the aromatic chromophore effects a rapid intramolecular energy transfer to the azido group, resulting in bond rupture and production of nitrene and nitrogen gas. The nitrogen that is released is in a vibrationally excited state, which may cause additional cellular injury.

The present invention also discloses a method of performing a phototherapeutic procedure using the disclosed sulfenate derivatives and their bioconjugates. An effective amount of sulfenate photosensitizer having the formula

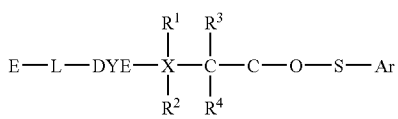

or the formula

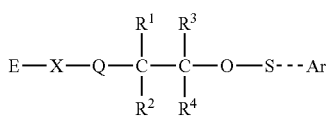

is administered to a subject.

When the sulfenate has the formula

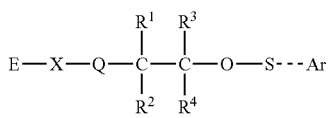

X is selected from the group consisting of —($R^5$)NOC—, —($R^5$)NOCCH$_2$O—, —($R^5$)NOCCH$_2$CH$_2$O—, and —HNC(=S)NH; and Q is either a single bond or an alkenyl, aromatic, or heteroaromatic radical derived from a compound selected from the group consisting of olefins, benzenes, naphthalenes, naphthoquinones, fluorines, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines.

When the sulfenate has the formula

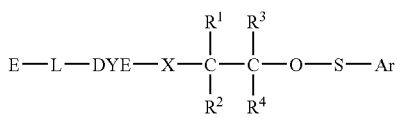

L and X are independently selected from the group consisting of —($R^5$)NOC—, —($R^5$)NOCCH$_2$O—, —($R^5$)NOCCH$_2$CH$_2$O—, —OCN($R^5$)—, —HNC(=S)NH—, and HNC(=O)NH—; and DYE is an aromatic or a heteroaromatic radical derived from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, indolenium dyes, crellins, and hypocrellins.

In all embodiments of sulfenates, E is selected from the group consisting of somatostatin receptor binding molecules, ST receptor binding molecules, neurotensin receptor binding molecules, bombesin receptor binding molecules, CCK receptor binding molecules, steroid receptor binding molecules, and carbohydrate receptor binding molecules, and dihydroxyindolecarboxylic acid;

$R^1$ to $R^5$ are independently selected from the group consisting of hydrogen, C1-C10 alkyl, C5-C10 aryl, C1-C10 polyhydroxyalkyl, and C1-C10 polyalkoxyalkyl;

Ar is an aromatic or heteroaromatic radical derived from the group consisting of benzenes, naphthalenes, naphthoquinones, diphenylmethanes, fluorenes, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines.

Following administration, the photosensitizer is allowed to accumulate in target tissue which is exposed to light of wavelength between 300 and 950 nm. This light has sufficient power and fluence rate to cause necrosis or apoptosis of the target tissue. The photoexcitation of the aromatic chromophore effects rapid intramolecular energy transfer to the sulfenate group, resulting in bond rupture and the production of two reactive free radicals which cause cellular injury.

In an alternative embodiment, the compounds of the present invention may be used to perform a phototherapeutic procedure in which a homogeneous photosensitizing mixture consisting of two or more Type 1 agents is prepared. This photosensitizing mixture is allowed to accumulate in target tissue which is exposed to light of wavelength between 300 and 950 nm with sufficient power and fluence rate to cause necrosis or apoptosis of the target tissue.

In another alternative embodiment, the compounds of the present invention may be used to perform a phototherapeutic procedure in which a homogeneous photosensitizing mixture consisting of two or more Type 2 (PDT) agents is prepared. This photosensitizing mixture is allowed to accumulate in target tissue which is exposed to light of wavelength between 300 and 950 nm with sufficient power and fluence rate to cause necrosis or apoptosis of the target tissue.

In a further alternative embodiment, the compounds of the present invention may be used to perform a phototherapeutic procedure in which a heterogeneous photosensitizing mixture consisting of one or more Type 1 agents and one or more Type 2 agents is prepared. This photosensitizing mixture is allowed to accumulate in target tissue which is exposed to light of wavelength between 300 and 950 nm with sufficient power and fluence rate to cause necrosis or apoptosis of the target tissue.

These and other embodiments of the inventive compounds and methods will be apparent in view of the following Figures, description, and examples.

DETAILED DESCRIPTION

Figure 1A:
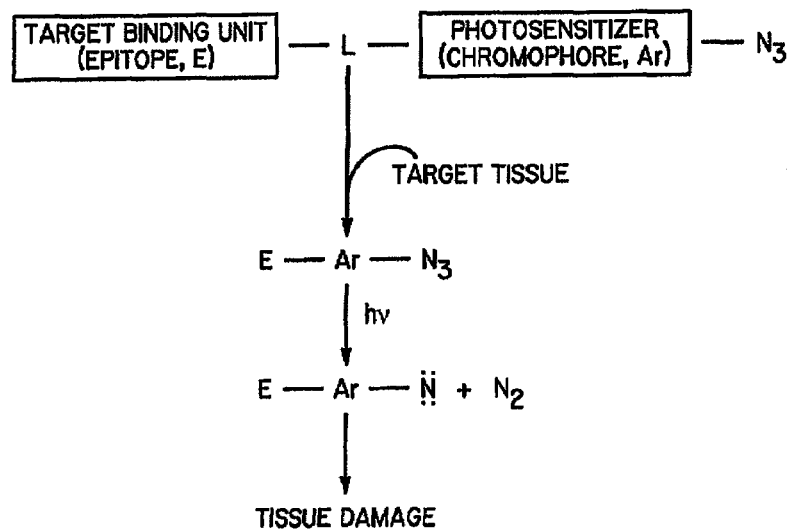
FIGS. 1A and 1B are schematic mechanisms for activation of the inventive azide compounds.
Figure 1:
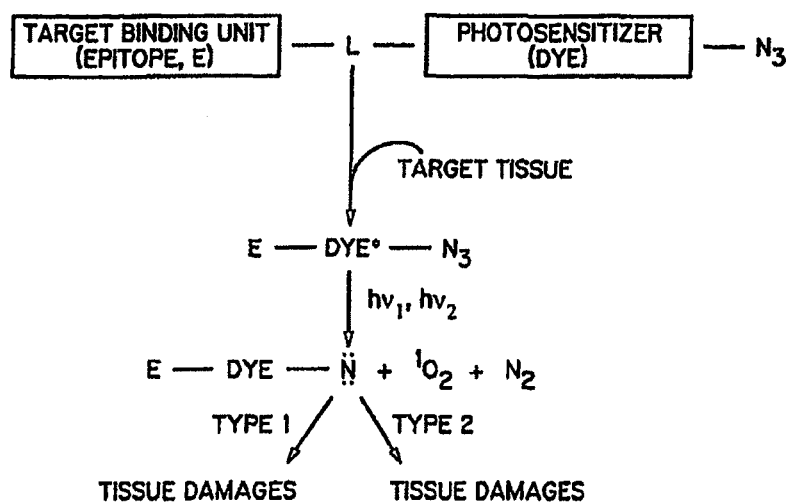
FIGS. 1C and 1D are schematic mechanisms for activation of the inventive sulfenate compounds.

In one embodiment, the present invention discloses novel compounds including organic azides, for phototherapy of tumors and other lesions, having the formula

E-L-DYE-X—$N_3$

DYE is an aromatic or a heteroaromatic radical derived from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, and indolenium dyes.

In one embodiment, the present invention discloses novel organic azide derivatives and their bioconjugates, for phototherapy of tumors and other lesions, having the formula

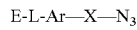

E-L-Ar—X—$N_3$

Ar is a chromophore that undergoes sensitization. This chromophore (Ar) is an aromatic or a heteroaromatic radical derived from the group consisting of benzenes, polyfluorobenzenes, naphthalenes, naphthoquinones, anthracenes, anthraquinones, phenanthrenes, tetracenes, naphthacenediones, pyridines, quinolines, isoquinolines, indoles, isoindoles, pyrroles, imidiazoles, pyrazoles, pyrazines, purines, benzimidazoles, benzofurans, dibenzofurans, carbazoles, acridines, acridones, phenanthridines, thiophenes, benzothiophenes, dibenzothiophenes, xanthenes, xanthones, flavones, coumarins, and anthacylines.

In all azide embodiments, $N_3$ is the azide moiety that produces nitrene upon photoactivation, i.e., a photoactive component;

L is a linker, i.e., linking unit or component, between the DYE or chromophore and the targeting moiety E epitope that targets the compound to a particular anatomical and/or physiological site in a patient, and is selected from the group consisting of —$(CH_2)_a$—, —$(CH_2)_b CONR^1$—, —$N(R^2)CO(CH_2)_c$—, —$OCO(CH_2)_d$—, —$(CH_2)_e CO_2$—, —OCONH—, —$OCO_2$—, —HNCONH—, —HNCSNH—, —HNNHCO—, —$OSO_2$—, —$NR^3(CH_2)_e CONR^4$—, —$CONR^5(CH_2)_f NR^6 CO$—, and —$NR^7 CO(CH_2)_g CONR^8$—;

X is a linking component that is either a single bond or is selected from the group consisting of —$(CH_2)_h$—, —OCO—, —HNCO—, —$(CH_2)_i CO$—, and —$(CH_2)_j OCO$—;

$R^1$ to $R^8$ are independently selected from the group consisting of hydrogen, C1-C10 alkyl, —OH, C1-C10 polyhydroxyalkyl, C1-C10 alkoxyl, C1-C10 alkoxyalkyl, —$SO_3 H$, —$(CH_2)_k CO_2 H$, and —$(CH_2)_l NR^9 R^{10}$;

$R^9$ and $R^{10}$ are independently selected from the group consisting of hydrogen, C1-C10 alkyl, C5-C10 aryl, and C1-C10 polyhydroxyalkyl;

a to l independently range from 0 to 10;

and the targeting moiety E epitope is selected from the group consisting of somatostatin receptor binding molecules, ST receptor binding molecules, neurotensin receptor binding molecules, bombesin receptor binding molecules, cholecystekinin (CCK) receptor binding molecules, steroid receptor binding molecules, and carbohydrate receptor binding molecules.

In one embodiment, the present invention discloses novel sulfenate derivatives and their bioconjugates, for phototherapy of tumors and other lesions, having the formula

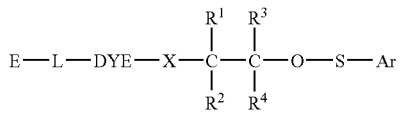

In one embodiment, the present invention discloses novel aromatic sulfenates, that react mainly by a type 1 mechanism for phototherapy of tumors and other lesions, having the formula

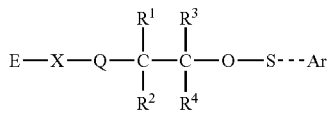

In all embodiments of sulfenates,

E is selected from the group consisting of somatostatin receptor binding molecules, ST receptor binding molecules, neurotensin receptor binding molecules, bombesin receptor binding molecules, cholecystekinin receptor binding molecules, steroid receptor binding molecules, and carbohydrate receptor binding molecules, and dihydroxyindolecarboxylic acid;

Ar is an aromatic or heteroaromatic radical derived from the group consisting of benzenes, naphthalenes, naphthoquinones, diphenylmethanes, fluorenes, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines.

When the sulfenate has the formula

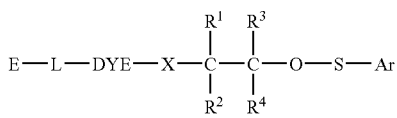

L and X are independently selected from the group consisting of —(R$^5$)NOC—, —(R$^5$)NOCCH$_2$O—, —(R$^5$)NOCCH$_2$CH$_2$O—, —OCN(R$^5$)—, —HNC(=S)NH—, and HNC(=O)NH—; and DYE is an aromatic or a heteroaromatic radical derived from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, indolenium dyes, crellins, and hypocrellins.

When the sulfenate has the formula

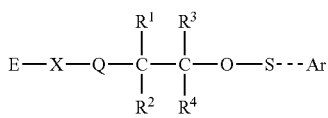

X is selected from the group consisting of —(R$^5$)NOC—, —(R$^5$)NOCCH$_2$O—, —(R$^5$)NOCCH$_2$CH$_2$O—, and —HNC(=S)NH; and Q is either a single bond or an alkenyl, aromatic, or heteroaromatic radical derived from a compound selected from the group consisting of olefins, benzenes, naphthalenes, naphthoquinones, fluorines, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines.

In all embodiments of sulfenates, R$^1$ to R$^5$ are independently selected from the group consisting of hydrogen, C1-C10 alkyl, C5-C10 aryl, C1-C10 polyhydroxyalkyl, and C1-C10 polyalkoxyalkyl.

The present invention also discloses a method of performing a therapeutic procedure using the disclosed azide compounds. An effective amount of organic azide photosensitizer is administered to a subject, where the organic azide photosensitizer has the formula

E-L-DYE-X—N$_3$ where DYE is an aromatic or a heteroaromatic radical derived from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, and indolenium dyes; or the formula E-L-Ar—X—N$_3$ where Ar is an aromatic or a heteroaromatic radical derived from the group consisting of benzenes, polyfluorobenzenes, naphthalenes, naphthoquinones, anthracenes, anthraquinones, phenanthrenes, tetracenes, naphthacenediones, pyridines, quinolines, isoquinolines, indoles, isoindoles, pyrroles, imidiazoles, pyrazoles, pyrazines, purines, benzimidazoles, benzofurans, dibenzofurans, carbazoles, acridines, acridones, phenanthridines, thiophenes, benzothiophenes, dibenzothiophenes, xanthenes, xanthones, flavones, coumarins, and anthacylines.

In all azide embodiments, E is a hydrogen atom or is selected from the group consisting of somatostatin receptor binding molecules, ST receptor binding molecules, neurotensin receptor binding molecules, bombesin receptor binding molecules, CCK receptor binding molecules, steroid receptor binding molecules, and carbohydrate receptor binding molecules;

L is selected from the group consisting of —(CH$_2$)$_a$—, —(CH$_2$)$_b$CONR$^1$—, —N(R$^2$)CO(CH$_2$)$_c$—, —OCO(CH$_2$)$_d$—, —(CH$_2$)$_e$CO$_2$—, —OCONH—, —OCO$_2$—, —HNCONH—, —HNCSNH—, —HNNHCO—, —OSO$_2$—, —NR$^3$(CH$_2$)$_e$CONR$^4$—, —CONR$^5$(CH$_2$)$_f$NR$^6$CO—, and —NR$^7$CO(CH$_2$)$_g$CONR$^8$—;

X is either a single bond or is selected from the group consisting of —(CH$_2$)$_h$—, —OCO—, —HNCO—, —(CH$_2$)$_i$CO—, and —(CH$_2$)$_j$OCO—

R$^1$ to R$^8$ are independently selected from the group consisting of hydrogen, C1-C10 alkyl, —OH, C1-C10 polyhydroxyalkyl, C1-C10 alkoxyl, C1-C10 alkoxyalkyl, —SO$_3$H, —(CH$_2$)$_k$CO$_2$H, and —(CH$_2$)$_l$NR$^9$R$^{10}$;

R$^9$ and R$^{10}$ are independently selected from the group consisting of hydrogen, C1-C10 alkyl, C5-C10 aryl, and C1-C10 polyhydroxyalkyl; and a to l independently range from 0 to 10.

Following administration, the photosensitizer is allowed to accumulate in target tissue which is exposed to a light of wavelength between 300 and 950 nm. This light has sufficient power and fluence rate to cause necrosis or apoptosis of the target tissue.

The present invention also discloses a method of performing a phototherapeutic procedure using the disclosed sulfenate derivatives and their bioconjugates. An effective amount of sulfenate photosensitizer having the formula

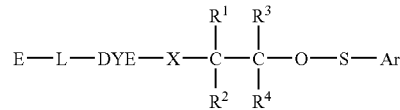

or the formula

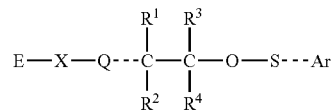

is administered to a subject.

When the sulfenate has the formula

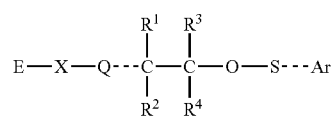

X is selected from the group consisting of —(R$^5$)NOC—, —(R$^5$)NOCCH$_2$O—, —(R$^5$)NOCCH$_2$CH$_2$O—, and —HNC(=S)NH; and Q is either a single bond or an alkenyl, aromatic, or heteroaromatic radical derived from a compound selected from the group consisting of olefins, benzenes, naphthalenes, naphthoquinones, fluorines, anthracenes, anthraquinones, phenanthrenes, tetracenes, naphthacenediones, pyridines, quinolines, isoquinolines, indoles, isoindoles, pyrroles, imidazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines.

When the sulfenate has the formula

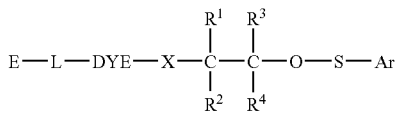

L and X are independently selected from the group consisting of —(R$^5$)NOC—, —(R$^5$)NOCCH$_2$O—, —(R$^5$) NOCCH$_2$CH$_2$O—, —OCN(R$^5$)—, —HNC(=S)NH—, and HNC(=O)NH—; and DYE is an aromatic or a heteroaromatic radical derived from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, indolenium dyes, crellins, and hypocrellins.

In all embodiments of sulfenates, E is selected from the group consisting of somatostatin receptor binding molecules, ST receptor binding molecules, neurotensin receptor binding molecules, bombesin receptor binding molecules, cholecystekinin receptor binding molecules, steroid receptor binding molecules, and carbohydrate receptor binding molecules, and dihydroxyindolecarboxylic acid;

$R^1$ to $R^5$ are independently selected from the group comprising hydrogen, C1-C10 alkyl, C5-C10 aryl, C1-C10 polyhydroxyalkyl, and C1-C10 polyalkoxyalkyl;

Ar is an aromatic or heteroaromatic radical derived from the group consisting of benzenes, naphthalenes, naphthoquinones, diphenylmethanes, fluorenes, anthracenes, anthraquinones, phenanthrenes, tetracenes, naphthacenediones, pyridines, quinolines, isoquinolines, indoles, isoindoles, pyrroles, imidazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines.

Following administration, the photosensitizer is allowed to accumulate in target tissue, which is exposed to light of wavelength between 300 and 950 nm with sufficient power and fluence rate to cause necrosis or apoptosis of the target tissue. The photoexcitation of the aromatic chromophore effects rapid intramolecular energy transfer to the sulfenate group, resulting in bond rupture and the production of two reactive free radicals which cause cellular injury.

In an alternative embodiment, the compounds of the present invention may be used to perform a phototherapeutic procedure whereby a homogeneous photosensitizing mixture consisting of two or more Type 1 agents is prepared. This photosensitizing mixture is allowed to accumulate in target tissue which is exposed to light of wavelength between 300 and 950 nm with sufficient power and fluence rate to cause necrosis or apoptosis of the target tissue.

In another alternative embodiment, the compounds of the present invention may be used to perform a phototherapeutic procedure whereby a homogeneous photosensitizing mixture consisting of two or more Type 2 (PDT) agents is prepared. This photosensitizing mixture is allowed to accumulate in target tissue which is exposed to light of wavelength between 300 and 950 nm with sufficient power and fluence rate to cause necrosis or apoptosis of the target tissue.

In a further alternative embodiment, the compounds of the present invention may be used to perform a phototherapeutic procedure whereby a heterogeneous photosensitizing mixture consisting of one or more Type 1 agents and one or more Type 2 agents is prepared. This photosensitizing mixture is allowed to accumulate in target tissue which is exposed to light of wavelength between 300 and 950 nm with sufficient power and fluence rate to cause necrosis or apoptosis of the target tissue.

In one embodiment, azides according to the present invention have the general formula

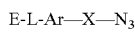

wherein Ar is an aromatic radical derived from the group consisting of benzenes, polyfluorobenzenes, anthracenes, anthraquinones, naphthacenediones, quinolines, isoquinolines, indoles, acridines, acridones, phenanthridines, xanthenes, xanthones, and anthacylines;

E is selected from the group consisting of somatostatin receptor binding molecules, ST receptor binding molecules, neurotensin receptor binding molecules, bombesin receptor binding molecules, cholecystekinin receptor binding molecule, steroid receptor binding molecules, and carbohydrate receptor binding molecules;

L is selected from the group consisting of —HNCO—, —CONR$^1$—, —HNCONH—, —HNCSNH—, —HNNHCO—, —(CH$_2$)$_a$CONR$^1$—, —CONR$^1$(CH$_2$)$_a$NR$^2$CO—, and —NR$^1$CO(CH$_2$)$_a$CONR$^2$—;

$R^1$ and $R^2$ are independently selected from the group consisting of hydrogen, C1-C10 alkyl, C1-C10 polyhydroxyalkyl; and a, b, and c independently range from 0 to 6.

In one embodiment, azides according to the present invention have the general formula

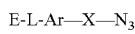

wherein Ar is selected from the group consisting of tetrafluorobenzenes, phenanthridines, xanthones, anthraquinones, acridines, and acridones;

E is a selected from the group consisting of octreotide and octreotate peptides, ST receptor binding peptides, carcinoembryonic antigen antibody (anti-CEA), bombesin receptor binding peptide, neurotensin receptor binding peptide, CCK receptor binding peptide, and estrogen steroids;

L is selected from the group consisting of —HNCO—, —CONR$^1$—, —HNCSNH—, —HNNHCO—, —(CH$_2$)$_a$ CONR$^1$—, —CONR$^1$(CH$_2$)$_a$NR$^2$CO—;

$R^1$ and $R^2$ are independently selected from the group consisting of hydrogen, C1-C10 alkyl, C1-C5 polyhydroxyalkyl; and a, b, and c independently range from 0 to 6.

The disclosed azide compounds operate mainly by a Type 1 mechanism as shown in FIGS. 1A and 1B. N$_3$ is the azide moiety that produces nitrene upon photoactivation, i.e., a photoactive component, and DYE or Ar (aromatic chromophore) undergoes photosensitization, i.e., a photoactive component. Aliphatic azido compounds can also be used for phototherapy, but may require high-energy light for activation unless the azide moiety is attached to conjugated polyene system. L is a linker (i.e., linking moiety or linking component) between DYE or Ar and the targeting moiety E epitope, which is a particular region of the molecule that is recognized by, and binds to, the target surface. E is usually, but not always, associated with biomolecules which include hormones, amino acids, peptides, peptidomimetics, proteins, nucleosides, nucleotides, nucleic acids, enzymes, carbohydrates, glycomimetics, lipids, albumins, mono- and polyclonal antibodies, receptors, inclusion compounds such as cyclodextrins, and receptor binding molecules. This targeting moiety targets the compound to a specific anatomical and/or physiological site in a patient. Specific examples of biomolecules include steroid hormones for the treatment of breast and prostate lesions, somatostatin receptor binding molecules, bombesin receptor binding molecules, and neurotensin receptor binding molecules for the treatment of neuroendocrine tumors, CCK receptor binding molecules for the treatment of lung cancer, ST receptor binding molecules and carcinoembryonic antigen (CEA) binding molecules for the treatment of colorectal cancer, dihyroxyindolecarboxylic acid and other melanin producing biosynthetic intermediates for melanoma, integrin receptor and atherosclerotic plaque binding molecules for the treatment of vascular diseases, and amyloid plaque binding molecules for the treatment of brain lesions. Examples of synthetic polymers include polyaminoacids, polyols, polyamines, polyacids, oligonucleotides, aborols, dendrimers, and aptamers.

Coupling of diagnostic and radiotherapeutic agents to biomolecules can be accomplished by methods well known in the art, as disclosed in Hnatowich et al., *Radioactive Labeling of Antibody: A simple and efficient method. Science*, 1983, 220, 613-615; Pelegrin et al., *Photoimmunodiagnosis with antibody-fluorescein conjugates: in vitro and in vivo pre clinical studies. Journal of Cellular Pharmacology*, 1992, 3, 141-145; and U.S. Pat. No. 5,714,342, each of which is expressly incorporated by reference herein in its entirety. Successful specific targeting of fluorescent dyes to tumors using antibodies and peptides for diagnostic imaging of tumors has been demonstrated by us and others, for example, in Achilefu et al., *Novel receptor-targeted fluorescent contrast agents for in vivo tumor imaging*, Investigative Radiology, 2000, 35(8), 479-485; Ballou et al., *Tumor labeling in vivo using cyanine conjugated monoclonal antibodies. Cancer Immunology and Immunotherapy*, 1995, 41, 257-263; and Licha et al., *New contrast agents for optical imaging: acid-cleavable conjugates of cyanine dyes with biomolecules. In Biomedical Imaging: Reporters, Dyes, and Instrumentation*, Bornhop, Contag, and Sevick-Muraca (Eds.), Proceedings of SPIE, 1999, 3600, 29-35, each of which is expressly incorporated by reference herein in its entirety. Therefore, the inventive receptor-targeted phototherapeutic agents are expected to be effective in the treatment of various lesions.

In the process outlined in FIGS. 1A and 1B for organic azide derivatives, the photoexcitation of the aromatic chromophore effects a rapid intramolecular energy transfer to the azido group, resulting in bond rupture and production of nitrene and nitrogen gas. The nitrogen that is released is in a vibrationally excited state, which may cause additional cellular injury.

Figure 1C:
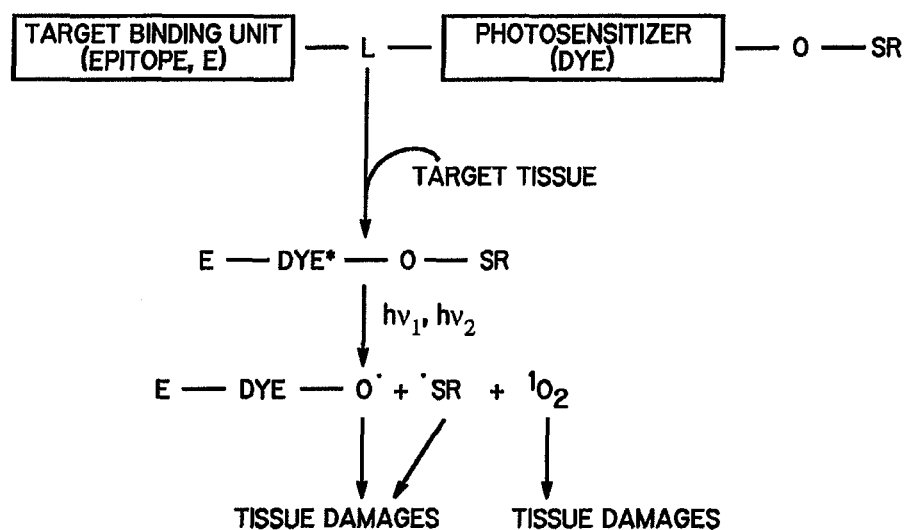
Figure 1D:
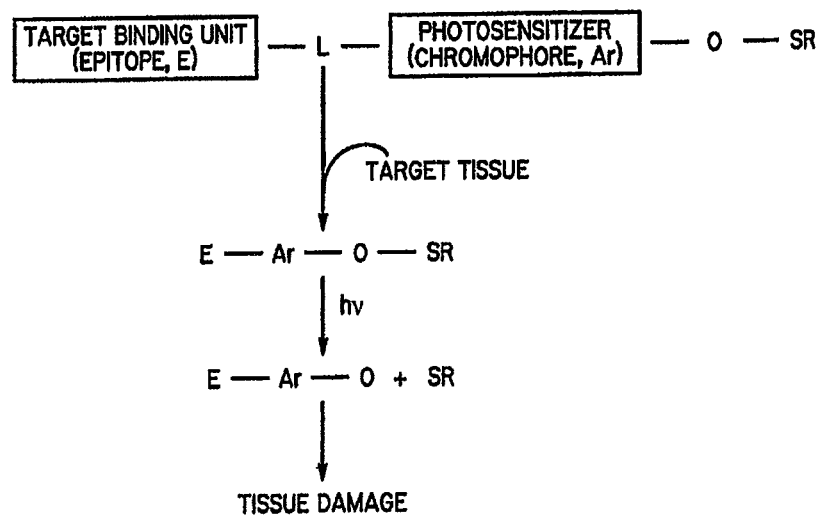

In the process outlined in FIGS. 1C and 1D for sulfenate derivatives, the photoexcitation of the aromatic chromophore effects rapid intramolecular energy transfer to the sulfenate group, resulting in bond rupture and production of two reactive free radicals which cause cellular injury.

The sulfenate compounds

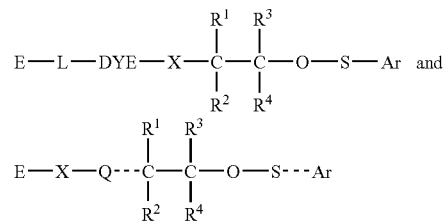

operate mainly by Type 1 mechanism as shown in FIGS. 1C and 1D respectively, wherein —O—SR is the sulfenate moiety that produces free radicals upon photoactivation, i.e., a photoactive component, and Ar is an aromatic chromophore that undergoes photosensitization, i.e., a photoactive component. Aliphatic sulfenates can also be used for phototherapy, but they are generally considered to be unstable and difficult to handle under ordinary conditions. Aliphatic and aromatic sulfenates can be used for phototherapy, although aromatic sulfenates have better material handling properties, as is known in the art (Amaudrut and Wiest, The thermal sulfenate-sulfoxide rearrangement: A radical pair mechanism. J. American Chemical Society, 2000, 122, 3367-3374, which is expressly incorporated by reference herein in its entirety). L is a linker, i.e., linking moiety or linking component, between the DYE or chromophore, i.e., photoactive component, and the epitope, i.e., targeting moiety or targeting component.

In the present invention, dual phototherapeutic effect involving both Type 1 and Type 2 mechanisms can be accomplished by incorporating the reactive intermediate precursors into conventional PDT dyes and using a dual wavelength light source to effect the generation of reactive intermediates as well as the generation of singlet oxygen. In some cases it may be possible to activate both Type 1 and Type 2 mechanisms using same wavelength of light. Dyes containing azide group have been prepared previously, as in Sunthankar et al., *Reactive disperse dyes. 1. Reactivity involving nitrene intermediate from azido group. Indian Journal of Chemistry*, 1973, 11(5), 503-504, which is expressly incorporated by reference herein in its entirety.

For all the described organic azo, azide, and sulfenate compounds, for targeting purposes, external attachment of an epitope E, i.e., targeting moiety or targeting component, is used to target the compound to a particular anatomical and/or physiological site in a patient. E is a particular region of the molecule that is recognized by, and binds to, the target site on the cell, i.e., a targeting component. E is usually, but not always, associated with biomolecules which include hormones, amino acids, peptides, peptidomimetics, proteins, nucleosides, nucleotides, nucleic acids, enzymes, carbohydrates, glycomimetics, lipids, albumins, mono- and polyclonal antibodies, receptors, inclusion compounds such as cyclodextrins, and receptor binding molecules. Specific examples of biomolecules include steroid hormones for the treatment of breast and prostate lesions, somatostatin receptor binding molecules, bombesin receptor binding molecules, and neurotensin receptor binding molecules for the treatment of neuroendocrine tumors, cholecystekinin receptor binding molecules for the treatment of lung cancer, ST receptor and carcinoembryonic antigen (CEA) binding molecules for the treatment of colorectal cancer, dihyroxyindolecarboxylic acid and other melanin producing biosynthetic intermediates for melanoma, integrin receptor and atherosclerotic plaque binding molecules for the treatment of vascular diseases, and amyloid plaque binding molecules for the treatment of brain lesions. Biomolecules for use in the present invention may also include synthetic polymers. Examples of synthetic polymers include polyaminoacids, polyols, polyamines, polyacids, oligonucleotides, aborols, dendrimers, and aptamers.

If the azo, azide, and/or sulfenate compounds themselves preferentially accumulate in the target tissue, however, an additional binding group may not be needed. For example, if Ar is an anthracycline moiety, it will bind to cancer cells directly and would not require an epitope for targeting purposes.

The azo, azide, and/or sulfenate derivatives of the present invention contain additional functionalities that can be used to attach various types of biomolecules, synthetic polymers, and organized aggregates for selective delivery to various organs or tissues of interest. The synthesis of typical dual phototherapeutic agents incorporating both Type 1 and Type 2 mechanisms based on phthalocyanine and cyanine derivatives for azide compounds are shown in FIGS. 2 and 3 respectively.

Figure 2:
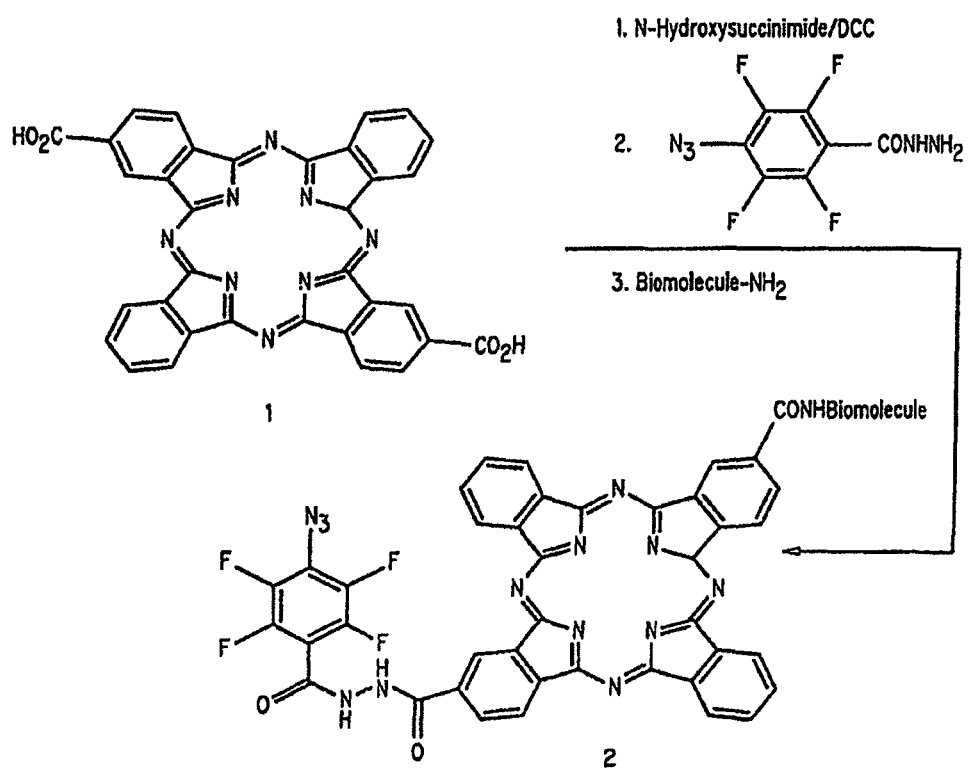
FIG. 2 is a schematic mechanism for the synthesis of a phthalocyanine azide derivative.
Figure 3:
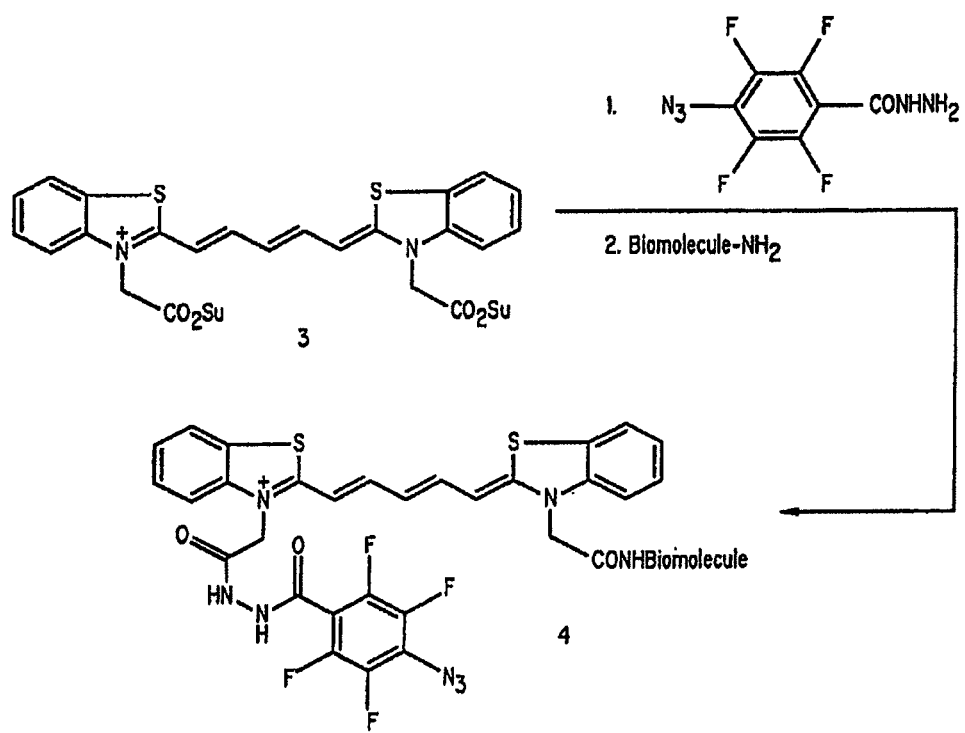
FIG. 3 is a schematic mechanism for the synthesis of a cyanine azide derivative.

Referring to FIG. 2, the diacid 1 can be prepared by the method analogous to phthalocyanine itself described previously in van Lier and Spikes, *The chemistry, photophysics, and photosensitizing properties of phthalocyanines*, In *Photosensitizing Compounds: Their Chemistry, Biology, and Clinical Use* (*Ciba Foundation Symposium* 146), Bock and Harnett (Eds.), J. Wiley & Sons, 1989, pp. 17-32, which is expressly incorporated by reference herein its entirety. The diacid 1 can be converted to the corresponding bis active ester in which one of the active esters can be condensed with an azide (by the Type 1 moiety) and the other active ester can be condensed with a biomolecule of interest to yield the phthalocyanine derivative 2. Referring to FIG. 3, the cyanine dye 3 is prepared by the alkylation of 2-methylbenzothiazole with N-succinimydyl bromoacetate followed by condensation with malonaldehyde tetramethyl acetal. One of the active esters in the cyanine dye 3 can be attached to a Type 1 moiety and the other ester can be attached to a biomolecule to give the dual phototherapeutic agent 4. Specifically, the biomolecules bind to colorectal, cervical, ovarian, lung, and neuroendocrine tumors, and include somatostatin receptor binding molecules, CCK receptor binding molecules, bombesin receptor binding molecules, neuroendrocrine receptor binding molecules, and ST receptor binding molecules. The other active ester can be conjugated to an aromatic or an aliphatic azides depending on the wavelength desired for excitation.

The synthesis of azido compounds is accomplished by a variety of methods known in the art, such as disclosed in Sandler and Karo, Azides in *Organic Functional Group Preparations* (*Second Ed.*), pp. 323-349, Academic Press: New York, 1986, which is expressly incorporated by reference herein in its entirety. Aromatic azides derived from acridone, xanthone, anthraquinone, phenanthridine, and tetrafluorophenyl systems have been shown to photolyze in the visible and in UV-A regions, e.g., Dyall and Ferguson, *Pyrolysis of aryl azides. XI Enhanced neighbouring group effects of carbonyl in a locked conformation. Australian J. Chem*, 1992, 45, 1991-2002; Kolendo, *Unusual product in the photolysate of 2-azidoxanthone. Chemistry of Heterocyclic Compounds*, 1998, 34(10), 1216; Theiler, *Effect of infrared and visible light on 2-azidoanthraquinone in the QA binding site of photosynthetic reaction centers. An unusual mode of activation of photoaffinity label. Biological Chemistry Hoppe-Seyler*, 1986, 367(12), 1197-207; Cantrell and Yielding, *Repair synthesis in human lymphocytes provoked by photolysis of ethidium azide. Photochemistry and Photobiology*, 1977, 25(2), 1889-191; and Pandurangi et al., *Chemistry of bifunctional photoprobes 3: correlation between the efficiency of CH insertion by photolabile chelating agents. First example of photochemical attachment of 99mTc complex with human serum albumin. J. Organic Chemistry*, 1998, 63, 9019-9030, each of which is expressly incorporated by reference herein in its entirety. The inventive azide derivatives contain additional functionalities that can be used to attach various types of biomolecules, synthetic polymers, and organized aggregates for selective delivery to various organs or tissues of interest. Preparations of representative compounds from embodiment are outlined in FIGS. 4-7.

Figure 4:
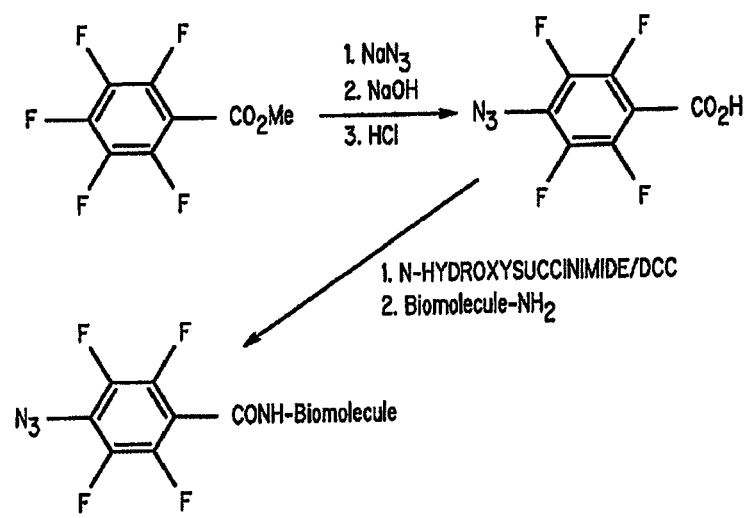
FIG. 4 is a schematic pathway for the synthesis of a tetrafluorophenylazide derivative.

A typical preparation of a tetrafluorophenylazide derivative is shown in FIG. 4. Methyl 2,3,4,5,6-pentafluorophenylbenzoate is reacted with sodium azide in aqueous acetone, and the resulting azidoester is saponified with sodium hydroxide to give 4-azido-2,3,5,6-tetrafluorobenzoic acid. The azidoacid is then converted to the corresponding active ester using N-hydroxysuccimide (NHS) and dicyclohexylcarbodiimide (DCC). The active ester can be attached to any desired biomolecule of interest. Specifically, the biomolecules bind to colorectal, cervical, ovarian, lung, and neuroendocrine tumors, and include somatostatin receptor binding molecules, CCK receptor binding molecules, bombesin receptor binding molecules, neuroendrocrine receptor binding molecules, and ST receptor binding molecules.

Figure 5:
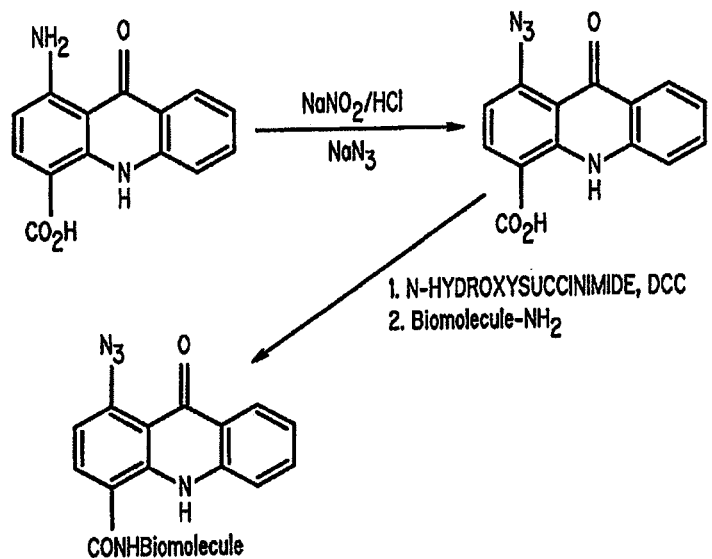
FIG. 5 is a schematic pathway for the synthesis of an acridone azide derivative.

An acridone derivative is prepared according to FIG. 5. The starting aminoacridone is converted to the azide by a standard method of diazotization of the amino group and displacement of the diazonium group with sodium azide, as disclosed in Matsumura, 1-*Aminoacridine-4-carboxylic acid. J. American Chem Society*, 1938, 32, 591-592, which is expressly incorporated by reference herein in its entirety. The azide is then conjugated to the biomolecules directly using an automated peptide synthesizer, or indirectly by the active ester route.

Figure 6:
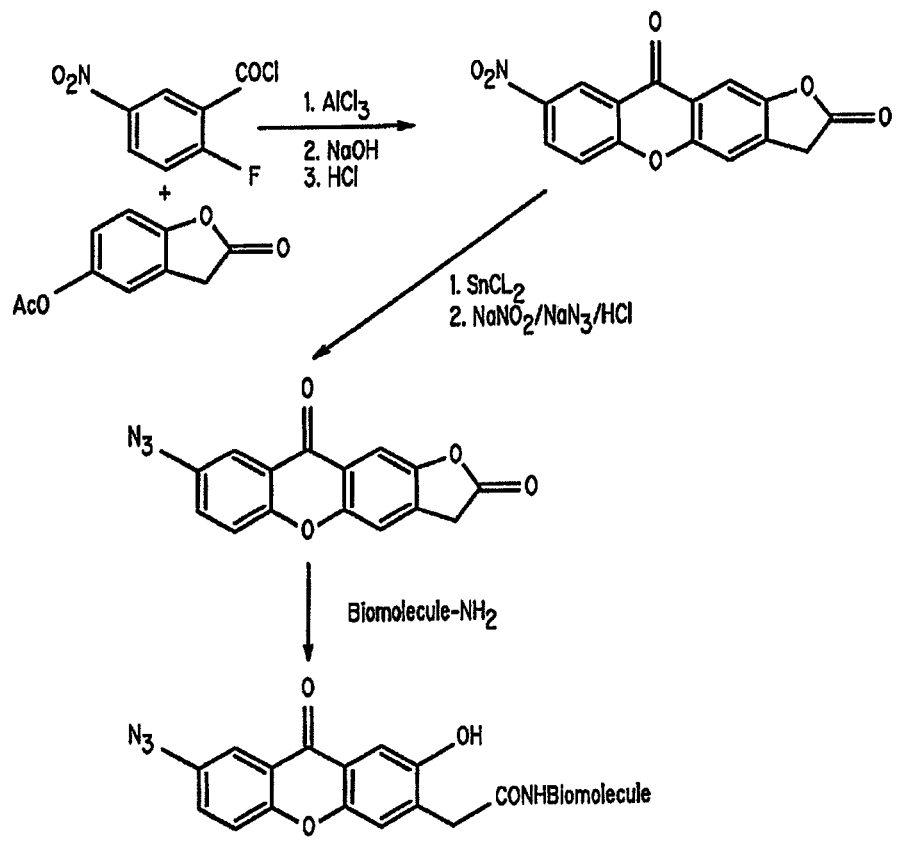
FIG. 6 is a schematic pathway for the synthesis of an azidoxanthone derivative.

A typical preparation of an azidoxanthone derivative is outlined in FIG. 6. The acid chloride is reacted with the lactone under Friedel-Crafts conditions to give the benzophenone intermediate, which is saponified and cyclized at once to the nitroxanthone. The nitro group is then converted to the azide by a standard sequence of reactions, that is, reduction, diazotization, and sodium azide treatment. The lactone ring should be sufficiently reactive for conjugation to biomolecules mentioned previously.

Figure 7:
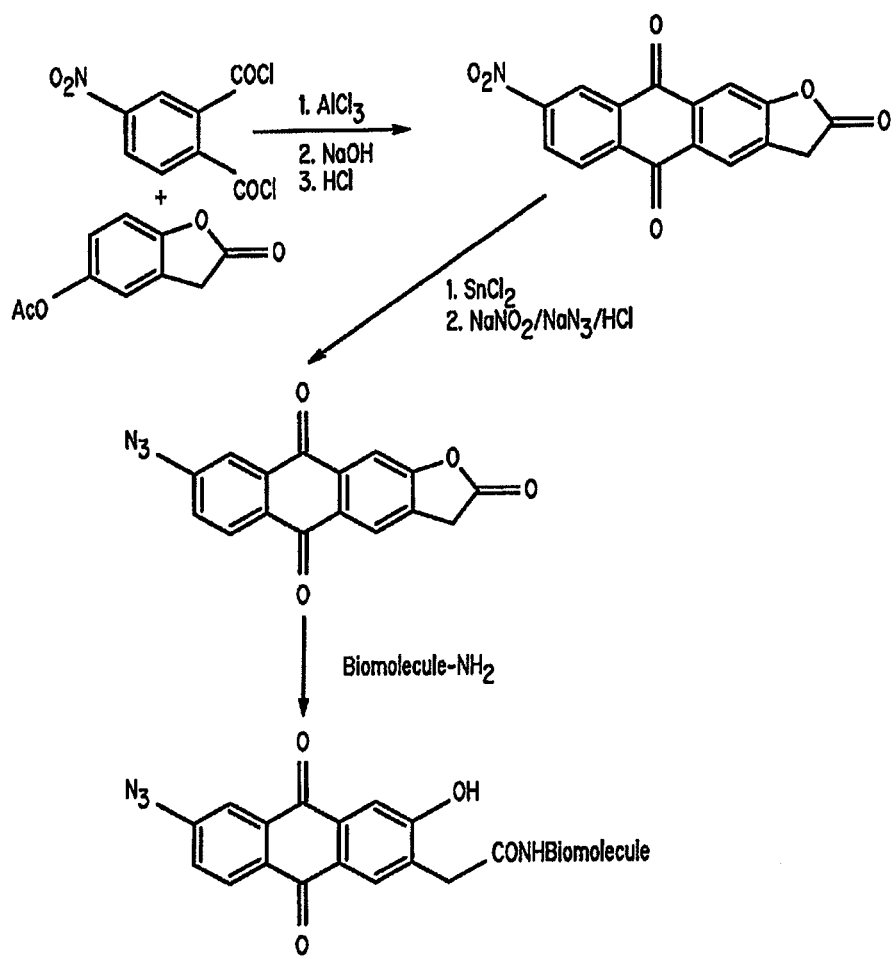
FIG. 7 is a schematic pathway for the synthesis of an azidoanthraquinone derivative.

Azidoanthraquinone derivatives can be synthesized according to FIG. 7. The diacid chloride is reacted with the lactone under Friedel-Crafts conditions to the corresponding nitroanthroquinone. The nitro group is then converted to the azido group by the standard procedure previously described. The lactone ring is sufficiently reactive for conjugation to the desired biomolecule or, alternatively, it could be hydrolyzed to the acid and then coupled to the biomolecule by conventional methods.

Figure 8:
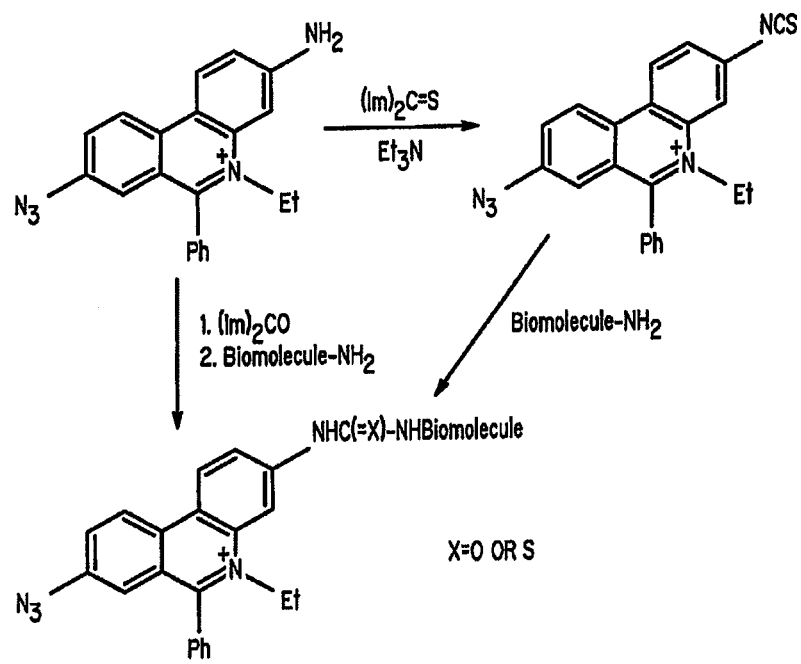
FIG. 8 is a schematic pathway for the synthesis of an azidophenanthridene derivative.

The azidophenanthridene derivatives can be prepared according to FIG. 8. Preparation of the starting material, ethidium azide, has been described in Cantrell and Yielding, *Binding of ethidium monoazide to the chromatin in human lymphocytes. Biochimica and Biophyica Acta*, 1980, 609(1), 173-179, which is expressly incorporated by reference herein in its entirety. The amino group can be activated in several ways. In particular, it can be converted to an isothiocyanate derivative using thiocarbonyl diimidazole or thiophosgene, or it can also be directly condensed with a biomolecule using disuccinimidyl carbonate or carbonyl diimidazole.

Figure 9:
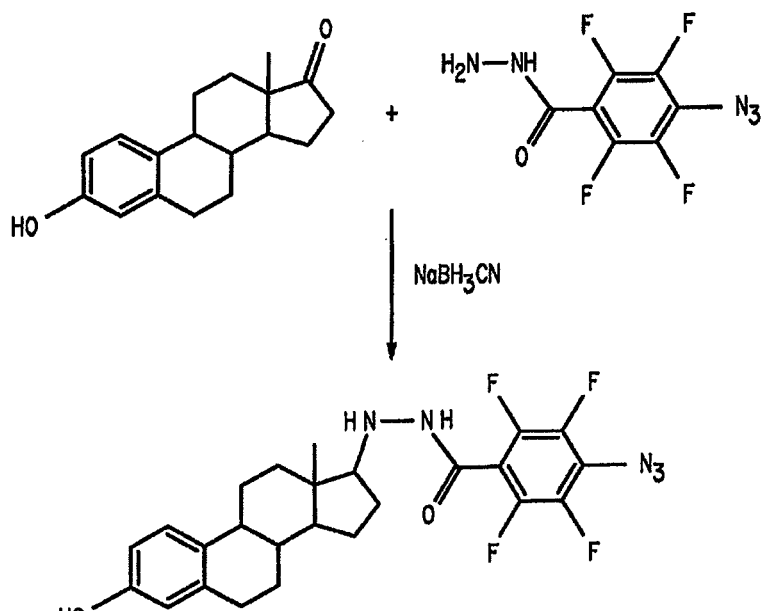
FIG. 9 is a schematic pathway for a steroid-azide photosensitizer conjugate.
Figure 10:
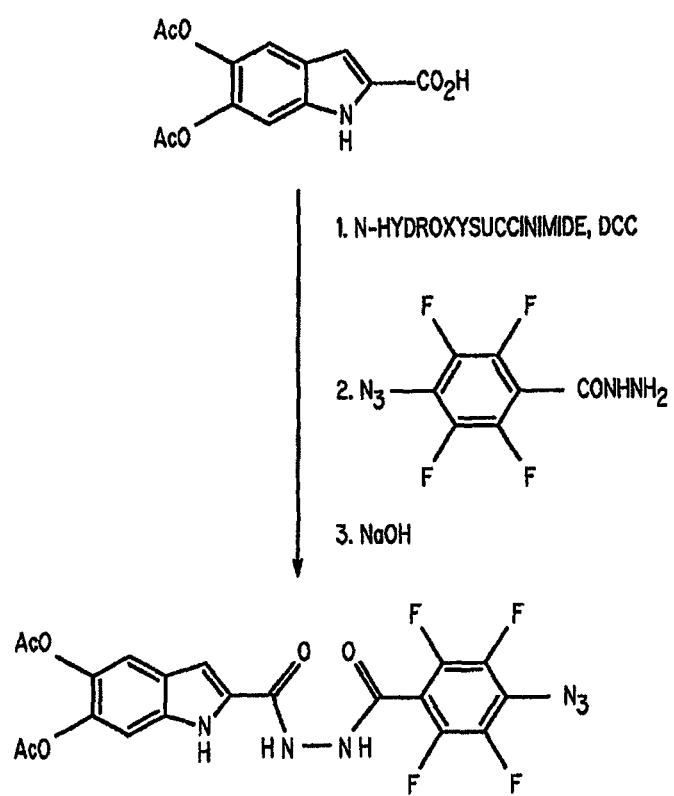
FIG. 10 is a schematic pathway for an azide photosensitizer attached to a biosynthetic intermediate.

A typical synthetic scheme of a steroid-photosensitizer conjugate using aromatic azides is shown in FIG. 9. As previously described, some compounds accumulate in tumors or other lesions without the assistance of a bioactive carrier. Administration of δ-aminolevulinic acid, an intermediate in porphyrin biosynthesis, results in a two-fold uptake of porphyrins in tumors compared to normal tissues. Similarly, administration of dihydroxyindole-2-carboxylic acid, an intermediate in melanin biosynthesis, produces substantially enhanced levels of melanin in melanoma cells compared to normal cells. Thus, a photosensitizer may be delivered to the site of lesion by attaching it to a biosynthetic intermediate, as shown in FIG. 10.

Figure 11:
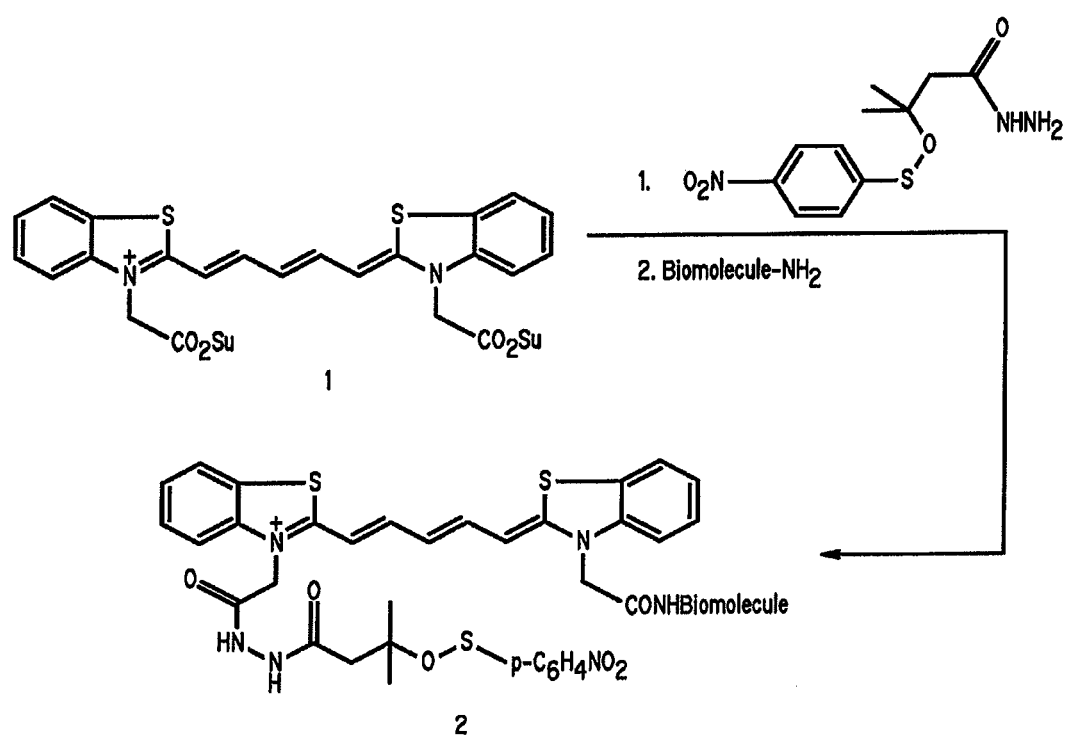
FIG. 11 is a schematic mechanism for the synthesis of a cyanine sulfenate derivative.
Figure 12:
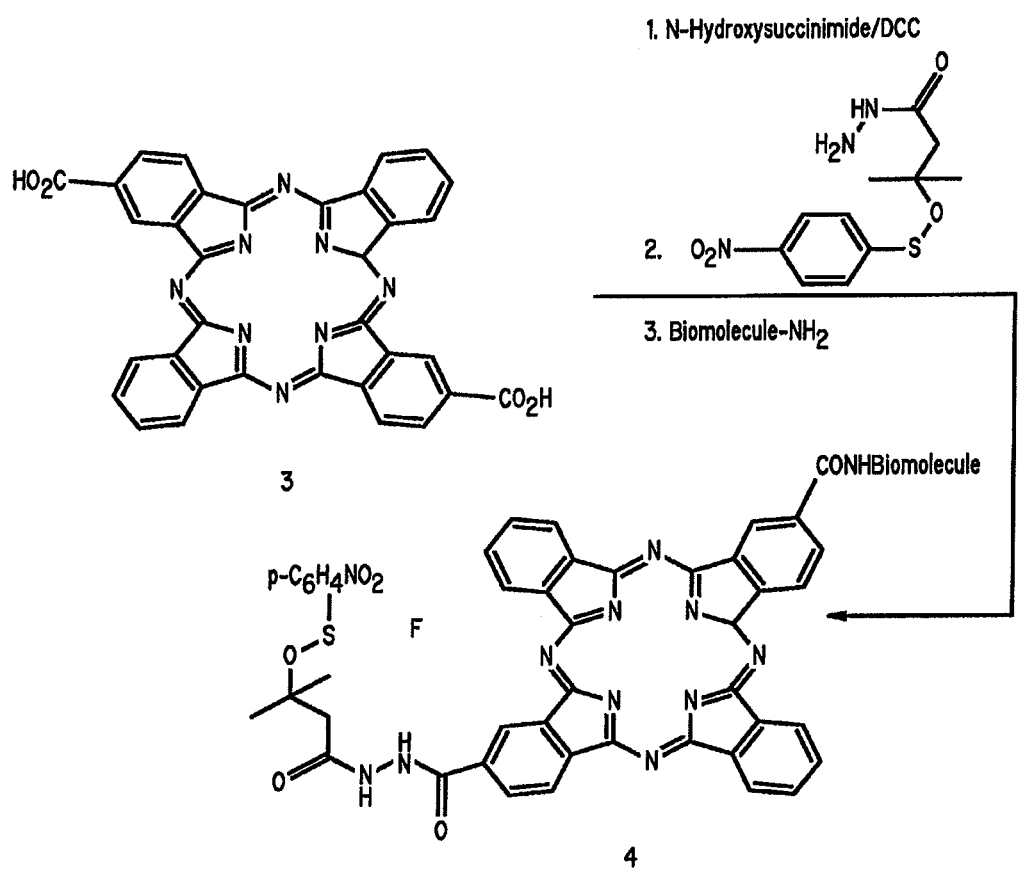
FIG. 12 is a schematic mechanism for the synthesis of a phthalocyanine sulfenate derivative.

The synthesis of sulfenate derivatives is accomplished by a method which generally involves the condensation of sulfenyl chlorides with alcohols in the presence of an organic base. This method is disclosed in Pasto and Cottard, *Demonstration of the synthetic utility of the generation of alkoxy radicals by the photo-induced, homolytic dissociation of alkyl 4-nitrobenzenesulfenates. Tetrahedron Letters*, 1994, 35(25), 4303-4306, which is expressly incorporated by reference herein in its entirety. The dye-sulfenate derivatives of the present invention contain additional functionalities that can be used to attach various types of biomolecules, synthetic polymers, and organized aggregates for selective delivery to various organs or tissues of interest. The synthesis of typical dual phototherapeutic agents incorporating both Type 1 and Type 2 mechanisms based on cyanine and phthalocyanine derivatives are shown in FIGS. 11 and 12. One of the active esters derived from either starting acid 1, 3 can be attached to a Type 1 moiety and the other active ester can be conjugated to any desired biomolecule of interest.

Figure 13:
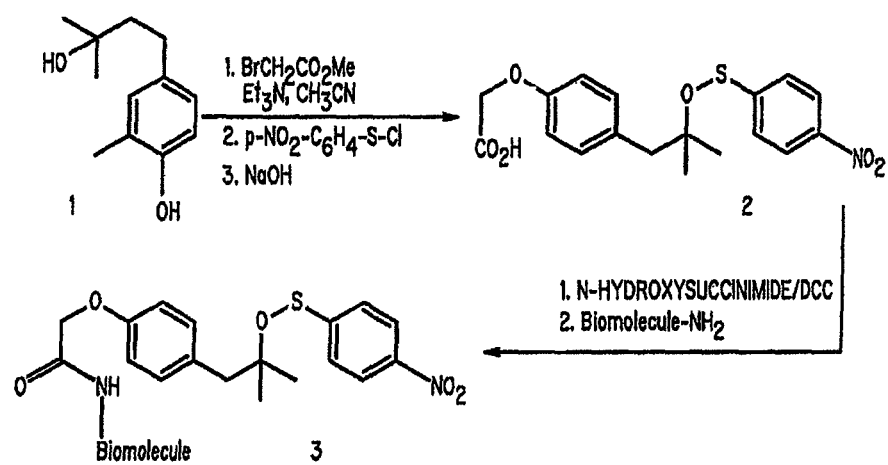
FIG. 13 is a schematic mechanism for the synthesis of a sulfenate diol.

A diol 1 is prepared by the reaction of methyl magnesium bromide with methyl 4-hydroxybenzoate. Referring to FIG. 13, alkylation of the resulting phenol with methyl bromoacetate, condensation of the tertiary alcohol with 4-nitrobenzenesulfenyl chloride, and saponification of the ester affords an intermediate acid 2. This acid 2 is then converted to the corresponding active ester using N-hydroxysuccimide (NHS) and dicyclohexylcarbodiimide (DCC). The active ester can be attached to any desired biomolecule of interest to form an aromatic sulfenate 3. Alternatively, the acid 2 can also be directly condensed with any biomolecule using automated peptide synthesizer.

Specifically, the biomolecule of the present invention pertains to those binding to colorectal, cervical, ovarian, lung, and neuroendocrine tumors. These include somatostatin receptor binding molecules, CCK receptor binding molecules, bombesin receptor binding molecules, neuroendrocrine receptor binding molecules, and ST receptor binding molecules.

Figure 14:
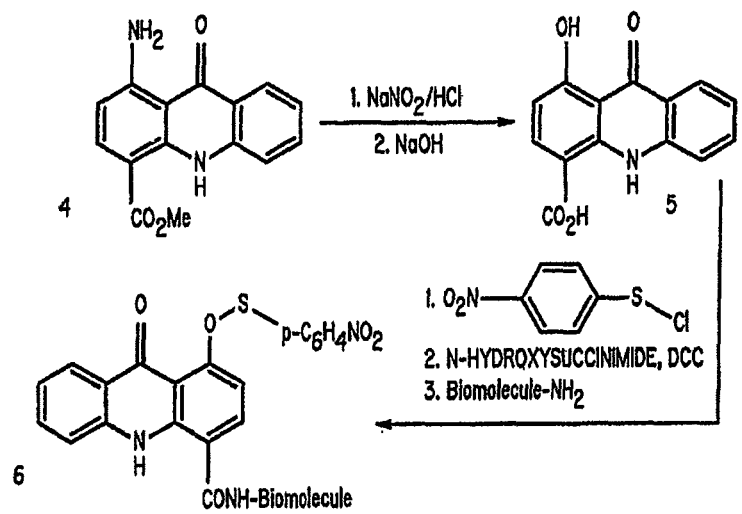
FIG. 14 is a schematic mechanism for the synthesis of an acridone sulfenate derivative.

An acridone derivative is prepared according to FIG. 14. The starting material 4 is prepared according to a standard method known to one of skill in the art, as disclosed in Matsumura, 1-Aminoacridine-4-carboxylic acid, J. American Chemical Society, 1938, 32, 591-592, which is expressly incorporated by reference herein in its entirety. An aminoacridone 4 is converted to a phenol by a standard method of diazotization of the amino group followed by displacement of the diazonium group with sodium hydroxide. The phenol 5 is converted to the corresponding p-nitrobenzenesulfenate and then conjugated to the biomolecules directly using an automated peptide synthesizer, or indirectly by the active ester route, to form the inventive acridine derivative 6.

Figure 15:
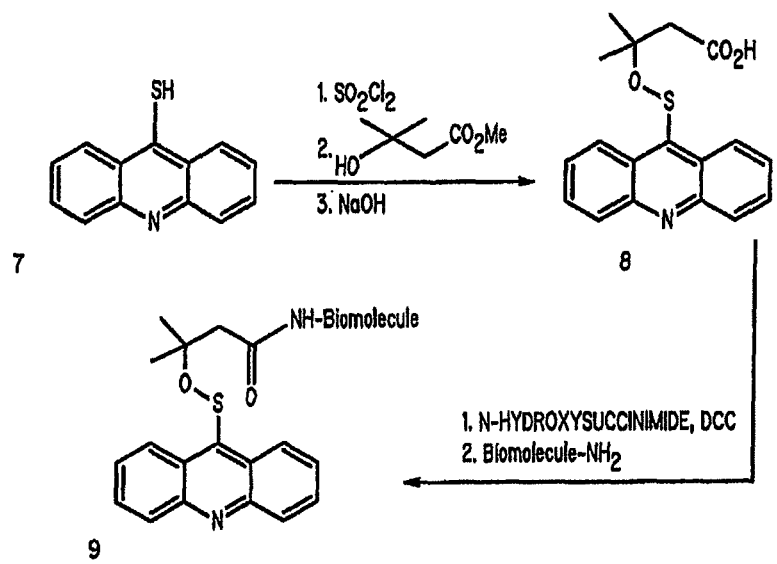
FIG. 15 is a schematic mechanism for the synthesis of an acridine sulfenate derivative.

A typical preparation of acridine-sulfenate derivative is outlined in FIG. 15. A thiol 7 is prepared from the known starting material 9-chloroacridone. It is converted to the corresponding sulfenyl chloride, condensed with methyl 3-hydroxy-3-methylbutyrate, and saponified to acid 8. The sulfenate-acid can be condensed with the desired biomolecules by the process previously described.

Figure 16:
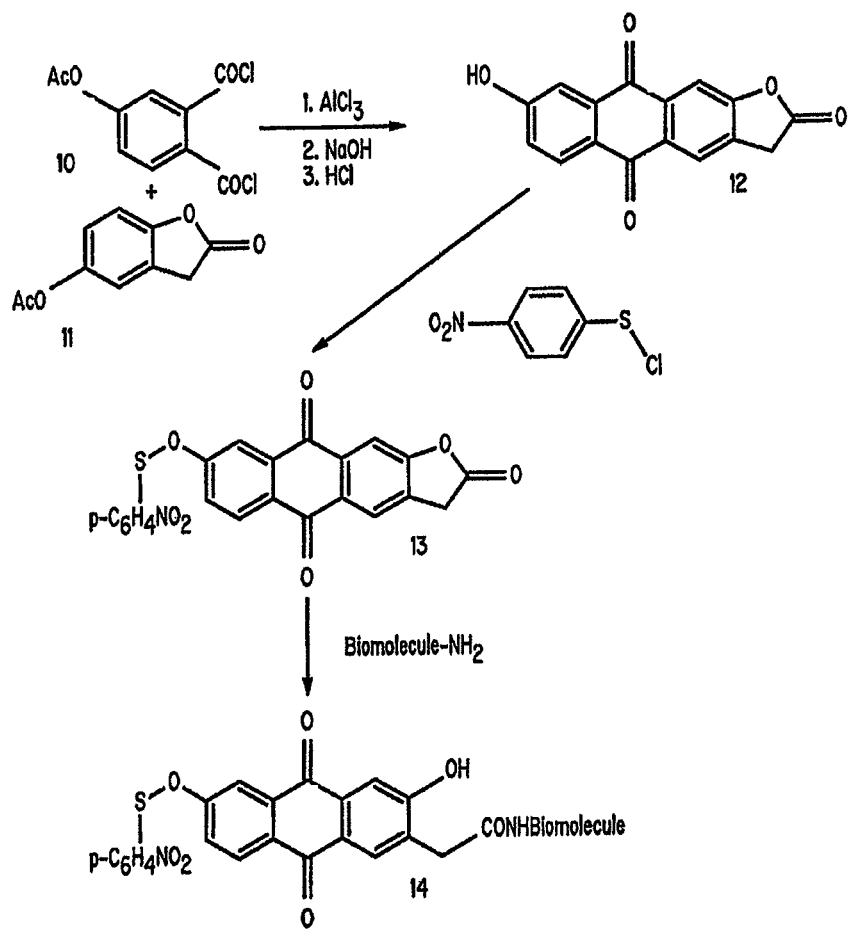
FIG. 16 is a schematic mechanism for the synthesis of an anthraquinone-sulfenate derivative.

The anthraquinone-sulfenate derivatives can be synthesized according to FIG. 16. A diacid chloride 10 is reacted with a lactone 11 under Friedel-Crafts conditions followed by saponification to the corresponding hydroxyanthraquinone 12. It is then condensed with p-nitrobenzenesulfenyl chloride and conjugated to the desired biomolecule directly to form an inventive derivative 14. Alternatively, the lactone 10 could be hydrolyzed to the acid and then coupled to the biomolecule by conventional methods.

Figure 17:
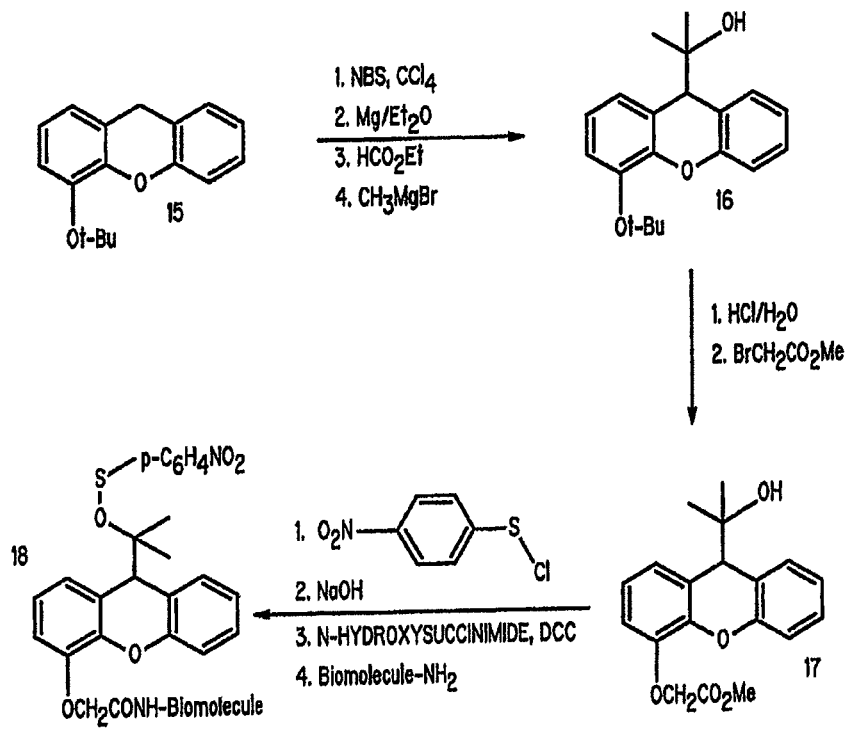
FIG. 17 is a schematic mechanism for the synthesis of a xanthene sulfenate derivative.

The xanthene derivative can be prepared according to FIG. 17. A xanthone benzyl ether 15 is prepared from the known 4-hydroxyxanthone by alkylation with benzylbromide. The compound 15 was converted to the ether 16 in three steps: bromination, Grignard reaction with ethylformate, and Grignard reaction with methylmagnesium bromide. Deprotection of the t-butyl group with HCl followed by alkylation with methyl bromoacetate provides a tertiary alcohol 17. The tertiary alcohol 17 is then condensed with p-nitrobenzenesulfenyl chloride, saponified, and conjugated to the desired biomolecules mentioned previously.

The novel compounds of the present invention may vary widely depending on the contemplated application. For tumors, the biomolecule is selected from the class of tumor markers including, but not limited to, somatostatin receptor binding molecules, bombesin receptor binding molecules, neurotensin receptor binding molecules, CCK receptor binding molecules, ST receptor binding molecules, estrogen receptor binding molecules, and progesterone receptor binding molecules. For vascular lesions, the biomolecule may be selected from the class of integrins, selecting, vascular endothelial growth factor, fibrins, tissue plasminogen activator, thrombin, LDL, HDL, Sialyl Lewisx and its mimics, and atherosclerotic plaque binding compounds.

Figure 18:
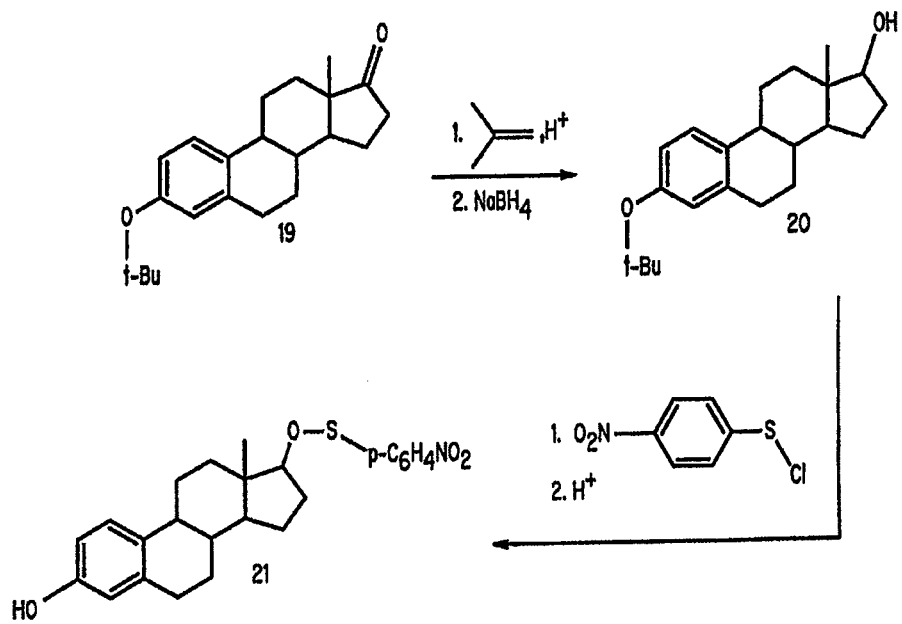
FIG. 18 is a schematic mechanism for the synthesis of a steroid-sulfenate photosensitizer conjugate.

A typical synthetic scheme of a steroid-photosensitizer conjugate is shown in FIG. 18. Estrone is protected as the t-butyl ether 19 and reduced with sodium borohydride to a mono protected estradiol 20, which is then condensed with p-nitrobenzenesulfenyl chloride. Deprotection of the t-butyl group yields the steroid-photosensitizer conjugate 21.

Figure 19:
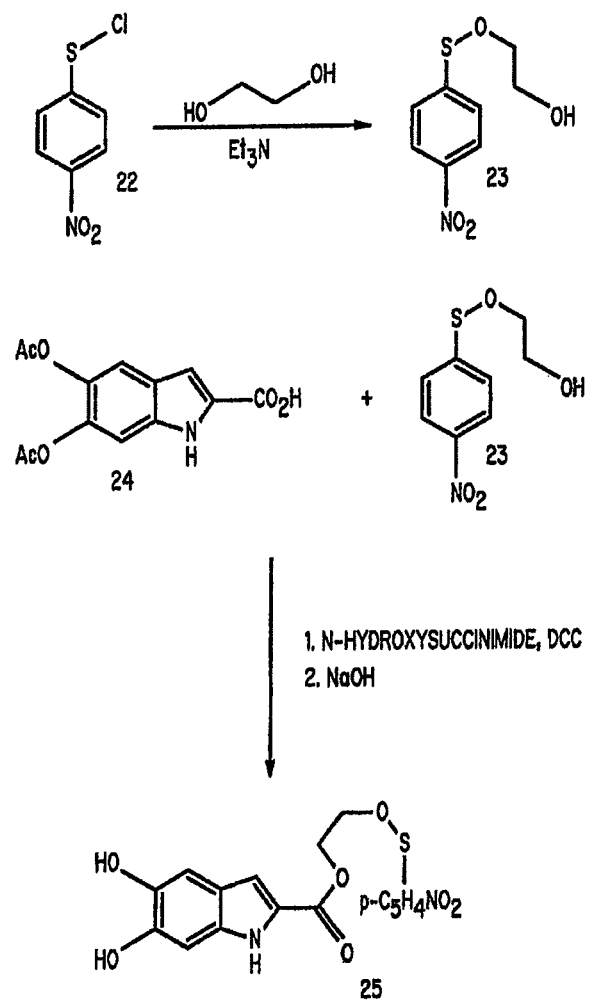
FIG. 19 is a schematic mechanism for delivering a sulfenate photosensitizer to the site of a lesion by attaching it to a biosynthetic intermediate.

As previously described, some compounds accumulate in tumors or other lesions without the assistance of a bioactive carrier. Administration of δ-aminolevulinic acid, an intermediate in porphyrin biosynthesis, results in a two-fold uptake of porphyrins in tumors compared to normal tissues. Similarly, administration of dihydroxyindole-2-carboxylic acid, an intermediate in melanin biosynthesis, produces substantially enhanced levels of melanin in melanoma cells compared to normal cells. Thus, a photosensitizer may be delivered to the site of lesion by attaching it to a biosynthetic intermediate, as shown in FIG. 19. The mono sulfenate 23 is prepared by the reaction of p-nitrobenzenesulfenyl chloride 22 with ethylene glycol and is condensed with an indole derivative 24. Hydrolysis of the diacetate provides the conjugate 25.

Methods of performing therapeutic procedures with the inventive compound are also disclosed. An effective amount of the inventive compound in a pharmaceutically acceptable formulation is administered to a patient. For example, parenteral administration advantageously contains a sterile aqueous solution or suspension of the photosensitizer in a concentration ranging from about 1 nM to about 0.5 M. In one embodiment, preferred parenteral formulations have a concentration of 1 pM to 10 mM photosensitizer. In one embodiment, parenteral formulation have a concentration of 1 μM to 10 mM photosensitizer. Such solutions also may contain pharmaceutically acceptable buffers, emulsifiers, surfactants, and, optionally, electrolytes such as sodium chloride. Formulations for enteral administration may vary widely, as is well known in the art. In general, such formulations are liquids, which include an effective amount of the complexes in aqueous solution or suspension. Such enteral formulations may optionally include buffers, surfactants, emulsifiers, thixotropic agents, and the like. Compounds for oral administration may also contain flavoring agents and other ingredients for enhancing their organoleptic qualities. Formulations for topical delivery may also contain liquid or semisolid excipients to assist in the penetration of the photosensitizer. The compounds may also be delivered in an aerosol spray.

The dose of the photosensitizer may vary from 0.1 to 500 mg/kg body weight, preferably from 0.5 to 2 mg/kg body weight. The photosensitizer is allowed to accumulate in the region of interest, followed by illumination with the light of wavelength 300 to 1200 nm, preferably 350 to 850 nm, at the site of the lesion. If the lesion is on the skin surface, the photosensitizer can be directly illuminated; otherwise, endoscopic catheters equipped with a light source may be employed to achieve phototherapeutic effect. The intensity, power, duration of illumination, and the wavelength of the light may vary widely depending on the location and site of the lesions. The fluence rate is preferably, but not always, kept below 200 mW/cm$^2$ to minimize thermal effects. Appropriate power depends on the size, depth, and the pathology of the lesion. The inventive compounds have broad clinical utility which includes, but is not limited to, phototherapy of tumors, inflammatory processes, and impaired vasculature.

The inventive compounds can be formulated into diagnostic or therapeutic compounds for enteral, parenteral, topical, or cutaneous administration. Topical or cutaneous delivery of the photosensitizer may also include aerosol formulation, creams, gels, solutions, etc. The compounds are administered in doses effective to achieve the desired diagnostic or therapeutic effect. Such doses may vary widely depending upon the particular complex employed, the organs or tissues to be examined, the equipment employed in the clinical procedure, the efficacy of the treatment achieved, and the like. These compounds contain an effective amount of the phototherapeutic agent, along with conventional pharmaceutical carriers and excipients appropriate for the type of administration contemplated. These compounds may also include stabilizing agents and skin penetration enhancing agents.

The following example illustrates a specific embodiment of the invention pertaining to the preparation and properties of a typical bioconjugate derived from bombesin, a bioactive peptide; 4-azido-2,3,5,6-tetrafluorophenylbenzoyl hydrazide, a Type 1 chromophore; and carboxymethylcyanine dye, a PDT chromophore.

Example 1

Synthesis of
4-azido-2,3,5,6-tetrafluorophenylbenzoate-bombesin
(7-14) conjugate The peptide was prepared by fluorenylmethoxycarbonyl (Fmoc) solid phase peptide synthesis strategy with a commercial peptide synthesizer from Applied Biosystems (Model 432A SYNERGY Peptide Synthesizer). The first peptide cartridge contained Wang resin pre-loaded with an amide resin on 25-μmole scale. The amino acid cartridges were placed on the peptide synthesizer and the product was synthesized from the C- to the N-terminal position. Coupling of the Fmoc-protected amino acids (75 μmol) to the resin-bound free terminal amine (25 μmol) was carried out with 2-(1H-benzo-triazol-1-yl)-1,1,3,3-tetramethyluronium hexafluoro-phosphate (HBTU, 75 μmol)/N-hydroxybenzotriazole (HOBt, 75 μmol). Each Fmoc protecting group on solid support was removed with 20% piperidine in dimethylformamide before the subsequent amino acid was coupled to it. The last cartridge contained 4-azido-2,3,5,6-tetrafluorobenzoic acid, which was successfully coupled to the peptide automatically, thus avoiding the need for post-synthetic manipulations.

After the synthesis was completed, the product was cleaved from the solid support with a cleavage mixture containing trifluoroacetic acid (85%):water (5%):phenol (5%):thioanisole (5%) for 6 hours. The peptide-azide conjugate was precipitated with t-butyl methyl ether and lyophilized in water:acetonitrile (2:3) mixture. The conjugate was purified by HPLC and analyzed with LC/MS, which indicated that the desired compound was obtained in 99% HPLC purity. The azido-bombesin (7-14) conjugate has the following molecular structure: p-azidotetrafluorobenzoyl-Gln-Trp-Ala-Val-Gly-His-Leu-Met-NH$_2$ molecular weight (electrospray mass spectrum): m/Z, 1358 (M+H).

The following example illustrates a specific embodiment of the invention pertaining to the preparation and properties of a typical bioconjugate derived from bombesin, a bioactive peptide, and a phototherapeutic molecule, sulfenate.

Example 2

Synthesis of Sulfenate-Bombesin (7-14) Conjugate

The peptide is prepared by fluorenylmethoxycarbonyl (Fmoc) solid phase peptide synthesis strategy with a commercial peptide synthesizer from Applied Biosystems (Model 432A SYNERGY Peptide Synthesizer). The first peptide cartridge contains Wang resin pre-loaded with an amide resin on 25-μmole scale. The amino acid cartridges are placed on the peptide synthesizer and the product is synthesized from the C- to the N-terminal position. Coupling of the Fmoc-protected amino acids (75 μmol) to the resin-bound free terminal amine (25 μmol) is carried out with 2-(1H-benzotriazol-1-yl)-1,1,3,3-tetramethyluronium hexafluorophosphate (HBTU, 75 μmol)/N-hydroxybenzotriazole (HOBt, 75 μmol). Each Fmoc protecting group on the solid support was removed with 20% piperidine in dimethylformamide before the subsequent amino acid was coupled to it. The last cartridge contains sulfenate acid, which is coupled to the peptide automatically, thus avoiding the need for post-synthetic manipulations.

After the synthesis is completed, the product is cleaved from the solid support with a cleavage mixture containing trifluoroacetic acid (85%):water (5%):phenol (5%):thioanisole (5%) for 6 hours. The peptide-sulfenate conjugate is precipitated with t-butyl methyl ether and lyophilized in water:acetonitrile (2:3) mixture. The conjugate is purified by HPLC and analyzed with LC/MS. The sulfenate-bombesin (7-14) conjugate has the following molecular structure: p-azidotetrafluorobenzoyl-Gln-Trp-Ala-Val-Gly-His-Leu-Met-NH$_2$.

The above-listed compounds are well known to those skilled in the art and general descriptions of the compounds and their synthesis are described in U.S. Pat. No. 6,180,085; Jori, *Far-red-absorbing photosensitizers: their use in the photodynamic therapy of tumours*, J. Photochem. Photobiol. A: Chem., 62, (1992), 371-378; Patonay and Antoine, *Near-Infrared Fluorogenic Labels: New Approach to an Old Problem*, Anal. Chem., 63:6, (1991) 321A-327A; and Jori and Reddi, *Second Generation Photosensitizers for the Photodynamic Therapy of Tumours*, in *Light in Biology and Medicine*, Volume 2 (ed. Douglas et al.), Plenum Press, New York,

What is claimed is:

1. A compound of the formula

E-L-DYE-X—Y for use in a medical phototherapeutic procedure, the compound used to cause at least one of necrosis or apoptosis of a target tissue, wherein:

DYE is a photoactive type 2 photodynamic therapy (PDT) agent that may further comprise a photoactive diagnostic agent, a photoactive type 1 phototherapeutic agent, another photoactive type 2 PDT agent, or a combination thereof wherein said type 2 PDT agent operates through a type 2 mechanism requiring formation of singlet oxygen for causing tissue damage;

Y is a photoactive type 1 phototherapeutic agent that may further comprise another photoactive type 1 phototherapeutic agent, a photoactive type 2 PDT agent, or a combination thereof wherein said type 1 phototherapeutic agent operates through a type 1 mechanism, does not require oxygen for tissue damage and comprises azide or sulfenate moities;

E is a targeting component for targeting the compound to an anatomical and/or physiological site of a patient;

L is a linking component for linking E to DYE where L is selected from the group consisting of —(CH$_2$)$_a$—, —(CH$_2$)$_b$CONR$^1$—, —N(R$^2$)CO(CH$_2$)$_c$—, —OCO(CH$_2$)$_d$—, —(CH$_2$)$_e$CO$_2$—, —OCONH—, —OCO$_2$—, —HNCONH—, —HNCSNH—, —HNNHCO—, —OSO$_2$—, —NR$^3$(CH$_2$)$_e$CONR$^4$—, —CONR$^5$(CH$_2$)$_f$NR$^6$CO—, and —NR$^7$CO(CH$_2$)$_g$CONR$^8$—; and X is a linking component for linking DYE to Y where X is selected from the group consisting of —(CH$_2$)$_h$—, —HNCO—, —(CH$_2$)$_i$CO—, and —(CH$_2$)$_j$OCO— where a to j independently range from 0 to 10.

2. A method of using a compound in a medical phototherapeutic procedure, the method comprising:

administering a compound to a patient; and exposing the administered compound to at least one of visible or infrared light while the compound is at least one of on or in the patient, the compound used to cause at least one of necrosis or apoptosis of a target tissue, wherein the compound is

E-L-DYE-X—Y wherein:

DYE is a photoactive type 2 photodynamic therapy (PDT) agent that may further comprise a photoactive diagnostic agent, a photoactive type 1 phototherapeutic agent, another photoactive type 2 PDT agent, or a combination thereof wherein said type 2 PDT agent operates through a type 2 mechanism requiring formation of singlet oxygen for causing tissue damage;

Y is a photoactive type 1 phototherapeutic agent that may further comprise another photoactive type 1 phototherapeutic agent, a photoactive type 2 PDT agent, or a combination thereof wherein said type 1 phototherapeutic agent operates through a type 1 mechanism, does not require oxygen for tissue damage and comprises azide or sulfenate moities;

E is a targeting component for targeting the compound to an anatomical and/or physiological site of a patient;

L is a linking component for linking E to DYE where L is selected from the group consisting of —(CH$_2$)$_a$—, —(CH$_2$)$_b$CONR$^1$—, —N(R$^2$)CO(CH$_2$)$_c$—, —OCO(CH$_2$)$_d$—, —(CH$_2$)$_e$CO$_2$—, —OCONH—, —OCO$_2$—, —HNCONH—, —HNCSNH—, —HNNHCO—, —OSO$_2$—, —NR$^3$(CH$_2$)$_e$CONR$^4$—, —CONR$^5$(CH$_2$)$_f$NR$^6$CO—, and —NR$^7$CO(CH$_2$)$_g$CONR$^8$—; and X is a linking component for linking DYE to Y where X is selected from the group consisting of —(CH$_2$)$_h$—, —OCO—, —HNCO—, —(CH$_2$)$_i$CO—, and —(CH$_2$)$_j$OCO—, the method resulting in combined type 1 and type 2 therapy where a to j independently range from 0 to 10.

* * * * *

UNITED STATES PATENT AND TRADEMARK OFFICE
CERTIFICATE OF CORRECTION

PATENT NO. : 8,658,433 B2  
APPLICATION NO. : 11/931683  
DATED : February 25, 2014  
INVENTOR(S) : Raghavan Rajagopalan et al.

Page 1 of 1

It is certified that error appears in the above-identified patent and that said Letters Patent is hereby corrected as shown below:

In the Claims:

In Claim 1, at Column 24, Lines 2 and 3 read:

"selected from the group consisting of $-(CH_2)_h-$, $-HNCO-$, $-(CH_2)_iCO-$, and $-(CH_2)_jOCO-$"

Should read:

-- selected from the group consisting of $-(CH_2)_h-$, $-OCO-$, $-HNCO-$, $-(CH_2)_iCO-$, and $-(CH_2)_jOCO-$ --

Signed and Sealed this  
Sixth Day of May, 2014

Michelle K. Lee  
*Deputy Director of the United States Patent and Trademark Office*